(12) United States Patent
Jegorov et al.

(10) Patent No.: US 8,618,309 B2
(45) Date of Patent: Dec. 31, 2013

(54) SUNITINIB AND SALTS THEREOF AND THEIR POLYMORPHS

(75) Inventors: Alexandr Jegorov, Dobra Voda (CZ);
Ales Gavenda, Ostrava-Lhotka (CZ);
Pavel Vraspir, Rymarov (CZ); Augusto Canavesi, Locate Varesino (CO) (IT);
Francesca Scarpitta, Ivrea (TO) (IT)

(73) Assignee: Teva Pharmaceutical Industries Ltd., North Wales, PA (US)

( * ) Notice: Subject to any disclaimer, the term of this patent is extended or adjusted under 35 U.S.C. 154(b) by 57 days.

(21) Appl. No.: 13/055,609

(22) PCT Filed: Jul. 23, 2009

(86) PCT No.: PCT/US2009/051530
§ 371 (c)(1),
(2), (4) Date: Jan. 24, 2011

(87) PCT Pub. No.: WO2010/011834
PCT Pub. Date: Jan. 28, 2010

(65) Prior Publication Data
US 2011/0118477 A1    May 19, 2011

Related U.S. Application Data

(60) Provisional application No. 61/137,005, filed on Jul. 24, 2008, provisional application No. 61/086,589, filed on Aug. 6, 2008, provisional application No. 61/087,859, filed on Aug. 11, 2008, provisional application No. 61/088,961, filed on Aug. 14, 2008, provisional application No. 61/088,998, filed on Aug. 14, 2008, provisional application No. 61/094,341, filed on Sep. 4, 2008, provisional application No. 61/097,592, filed on Sep. 17, 2008, provisional application No. 61/105,154, filed on Oct. 14, 2008, provisional application No. 61/108,078, filed on Oct. 24, 2008, provisional application No. 61/113,044, filed on Nov. 10, 2008, provisional application No. 61/141,385, filed on Dec. 30, 2008, provisional application No. 61/164,542, filed on Mar. 30, 2009, provisional application No. 61/177,717, filed on May 13, 2009.

(51) Int. Cl.
*C07D 209/12* (2006.01)

(52) U.S. Cl.
USPC .......................................................... 548/468

(58) Field of Classification Search
USPC .......................................................... 548/468
See application file for complete search history.

(56) References Cited

U.S. PATENT DOCUMENTS

| | | | |
|---|---|---|---|
| 6,573,293 B2 | 6/2003 | Tang et al. |
| 6,642,232 B2 | 11/2003 | Mattson et al. |
| 7,119,209 B2 | 10/2006 | Jin et al. |
| 7,125,905 B2 | 10/2006 | Tang et al. |
| 7,179,910 B2 | 2/2007 | Guan et al. |
| 2002/0156292 A1 | 10/2002 | Tang et al. |
| 2003/0069298 A1 | 4/2003 | Hawley et al. |
| 2003/0229229 A1 | 12/2003 | Jin et al. |
| 2006/0009510 A1 | 1/2006 | Havens et al. |
| 2007/0191458 A1 | 8/2007 | Hawley et al. |

FOREIGN PATENT DOCUMENTS

| | | |
|---|---|---|
| WO | WO 01/60814 | 8/2001 |
| WO | WO 03/016305 | 2/2003 |
| WO | WO 2004/024127 | 3/2004 |
| WO | WO 2004/075775 | 9/2004 |
| WO | WO 2005/053614 | 6/2005 |
| WO | WO 2006/120557 | 11/2006 |
| WO | WO 2009/067674 | 5/2009 |
| WO | WO 2009/067686 | 5/2009 |
| WO | WO 2009/104021 | 8/2009 |
| WO | WO 2009/128083 | 10/2009 |
| WO | WO 2010/023473 | 3/2010 |
| WO | WO 2010/023474 | 3/2010 |
| WO | WO 2010/041134 | 4/2010 |
| WO | WO 2011/033472 A1 | 3/2011 |

OTHER PUBLICATIONS

J.M. Manley, Early Amidation Approach to 3-[(4-Amido)Pyrrol-2-yl]-2-Indolinones, Journal Organic Chemistry, vol. 68, No. 16, pp. 6447-6450, (2003).

Sun et al. "Discovery of 5-[5-Fluoro-2-oxo-1,2-dihydroindol-(3Z)-ylidenemethyl)-2,4-dimethyl-1H-pyrrole-3-carboxylic Acid (2-Diethylaminoethyl)amide, a Novel Tyrosine Kinase Inhibitor Targeting Vascular Endothelial and Platelet-Derived Growth Factor Receptor Tyrosine Kinase" *J. Med. Chem.* vol. 46, p. 1116-1119, (2003).

Carey and Sundberg, Advanced Organic Chemistry, Part B: Reactions and Synthesis, Chapter 3, p. 164-180, (2001).

IPRP/Written Opinion dated Jan. 25, 2011, 10 pages.

*Primary Examiner* — Shawquia Young
(74) *Attorney, Agent, or Firm* — Arent Fox LLP

(57) ABSTRACT

Process for the preparation of sunitinib malate form I via sunitinib acetate and polymorphs of said intermediate.

5 Claims, 24 Drawing Sheets

SUNITINIB AND SALTS THEREOF AND THEIR POLYMORPHS

CROSS-REFERENCE TO RELATED APPLICATIONS

This application is a National Stage Application of PCT/US2009/051530, filed Jul. 23, 2009, which claims the benefit of U.S. Provisional Application Nos. 61/137,005, filed Jul. 24, 2008; 61/086,589, filed Aug. 6, 2008; 61/087,859, filed Aug. 11, 2008; 61/088,961, filed Aug. 14, 2008; 61/088,998, filed Aug. 14, 2008; 61/094,341, filed Sep. 4, 2008; 61/097,592, filed Sep. 17, 2008; 61/105,154, filed Oct. 14, 2008; 61/108,078, filed Oct. 24, 2008; 61/113,044, filed Nov. 10, 2008; 61/141,385, filed Dec. 30, 2008; 61/164,542, filed Mar. 30, 2009; 61/177,717, filed May 13, 2009, all of which are incorporated herein by reference.

FIELD OF THE INVENTION

The present invention relates to Sunitinib acetate polymorphs and of Sunitinib base, processes for preparation thereof and processes for the preparation of crystalline Sunitinib malate form 1.

BACKGROUND OF THE INVENTION

Sunitinib base, N-[2-(diethylamino) ethyl]-5-[(Z)-(5-fluoro-1,2-dihydro-2-oxo-3H-indol-3-ylidine)methyl]-2,4-dimethyl-1H-pyrrole-3-carboxamide, of the following formula:

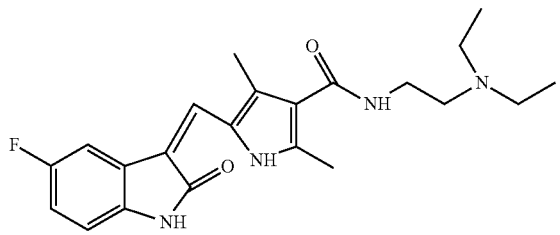 [SMILES: CCN(CC)CCNC(=O)c1c(C)[nH]c(/C=C2\C(=O)Nc3ccc(F)cc32)c1C]

can be used as an intermediate in the preparation of sunitinib salts, such as sunitinib malate of the following formula:

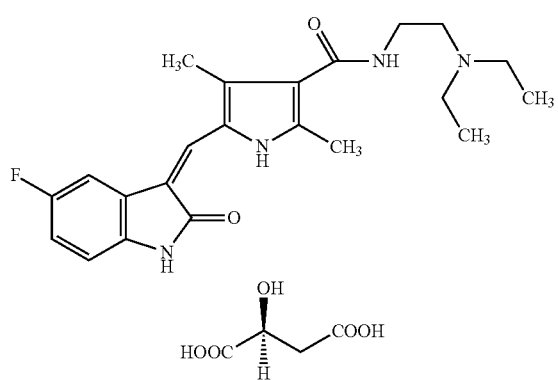

Sunitinib malate is a multi-kinase inhibitor marketed in the United States under the trade name SUTENT® by Pfizer, Inc. SUTENT® is approved by the FDA for the treatment of gastrointestinal stromal tumor after disease progression on or intolerance to imatinib mesylate and for the treatment of advanced renal cell carcinoma. SUTENT® is available as hard-shell capsules containing an amount of sunitinib malate that is equivalent to 12.5 mg, 25 mg, or 50 mg of sunitinib. The capsules contain sunitinib malate together with the inactive ingredients mannitol, croscarmellose sodium, povidone (K-25) and magnesium stearate.

U.S. Pat. No. 6,573,293 ("293 patent") refers to the preparation of sunitinib base and salts thereof, as well as the use of these salts. The '293 patent refers to the synthesis of sunitinib base by condensing 5-formyl-2,4-1H-pyrrole-3-carboxylic acid (2-diethylaminoethyl)amide with 5-fluoro-1,3-dihydro-indol-2-one in ethanol in the presence of pyrrolidine. See '293 patent, col. 204, ll. 33-50 (example 80, alternative synthesis). The sunitinib base thus prepared was isolated from the reaction mixture by filtration, washed with ethanol, slurried in ethanol, isolated from the slurry by filtration, washed with ethanol, and dried under vacuum to give an orange solid. See id.

U.S. Pat. No. 7,119,209 ("'209 patent") also refers to the preparation of sunitinib base. The '209 patent refers to the preparation of sunitinib base by reacting 4-(1H-imidazol-1-ylcarbonyl)-3,5-dimethyl-1H-pyrrole-2-carbaldehyde, N,N-diethylethylenediamine, and 5-fluorooxindole in acetonitrile in the presence of triethylamine. See '209 patent, col. 15, ll. 1-36. The sunitinib base thus prepared was isolated from the reaction mixture by filtration, washed with acetonitrile, and dried under vacuum.

U.S. Publication No. 2003/0069298 and U.S. Publication No. 2007/0191458 refer to the preparation of sunitinib L-malate by reacting Sunitinib base, L-malic acid and a solvent. In addition, it is also disclose forms I (also referred to herein as "Form 1") and II thereof.

Crystalline sunitinib malate form I is characterized by diffraction peaks at about 13.2 and 24.2 degrees two-theta, and more preferably, at about 13.2, 19.4, 24.2 and 25.5 degrees two-theta, and most preferably, as listed at table 1 for crystal form 1, in a powder X-ray diffraction pattern.

| Crystal Form I | |
|---|---|
| Two Theta (deg.) | Relative Intensity |
| 11.39 | 7 |
| 11.90 | 7 |
| 13.16 | 82 |
| 15.92 | 27 |
| 16.79 | 25 |
| 17.18 | 24 |
| 19.40 | 76 |
| 20.30 | 20 |
| 21.26 | 31 |
| 21.68 | 28 |
| 22.13 | 48 |
| 22.91 | 21 |
| 24.17 | 100 |
| 25.46 | 79 |
| 26.06 | 23 |
| 26.96 | 26 |
| 27.56 | 28 |

The present invention offers: a new salt of Sunitinib, Sunitinib acetate, which can be used as a useful intermediate for the preparation of Sunitinib malate; processes for preparation thereof and its conversion to crystalline Sunitinib malate form 1. In addition, the present invention offers other processes for the preparation of Sunitinib malate form 1.

SUMMARY OF THE INVENTION

In one embodiment, Sunitinib malate form 1 can be prepared by a process comprising reacting Sunitinib base, a weak acid and L-malic acid in alcohol or a mixture of water and alcohol, and precipitating the said crystalline form 1 of Sunitinib malate.

In another embodiment, the present invention encompasses Sunitinib acetate.

In yet another embodiment, the present invention encompasses a crystalline form of Sunitinib acetate characterized by data selected from a group consisting of a PXRD pattern having peaks at about 5.1, 9.6, 10.2, 12.8 and 16.9±0.2 degrees 2-theta, a PXRD pattern as depicted in FIG. 12, a solid-state $^{13}$C NMR spectrum having signals at about 165.2, 134.5, 130.4, 118.7, 115.7, 112.5 and 110.9±0.2 ppm, a solid-state $^{13}$C NMR spectrum having chemical shifts differences between the signal exhibiting the lowest chemical shift and another in the chemical shift range of 100 to 180 ppm of about 63.6, 32.9, 28.8, 17.1, 14.1, 10.8 and 9.2±0.1 ppm, a solid-state $^{13}$C NMR spectrum depicted in FIG. 20 and a combination thereof.

In one embodiment, the present invention encompasses a crystalline form of Sunitinib acetate characterized by data selected from a group consisting of: a PXRD pattern having peaks at about 6.1, 11.0, 15.8, 16.4 and 20.2±0.2 degrees 2-theta, a PXRD pattern as depicted in FIG. 17, a solid-state $^{13}$C NMR spectrum having signals at about 166.1, 133.0, 119.0, 114.5, 109.9 and 108.6±0.2 ppm, a solid-state $^{13}$C NMR spectrum having chemical shifts differences between the signal exhibiting the lowest chemical shift and another in the chemical shift range of 100 to 180 ppm of about 65.0, 31.9, 17.9, 13.4, 8.8 and 7.5±0.1 ppm, a solid-state $^{13}$C NMR spectrum depicted in FIG. 21 and a combination thereof.

In another embodiment, the present invention encompasses the use of the above of Sunitinib acetate and crystalline forms thereof to prepare sunitinib malate.

In yet another embodiment, the present invention encompasses a process for preparing Sunitinib malate comprising preparing crystalline Sunitinib acetate according to the processes of the present invention and converting it to Sunitinib malate.

In one embodiment, the invention encompasses a process for preparing crystalline sunitinib malate characterized by diffraction peaks at about 13.2 and 24.2 degrees two-theta comprising providing a mixture comprising sunitinib malate and a solvent selected from the group consisting of pyridine, dioxane, butyl acetate, ethyl acetate, dimethylformamide, a mixture of dimethylacetamide and n-propanol, a mixture of N-methyl-pyrrolidone ("NMP") and toluene, dimethylsulfoxide ("DMSO"), a mixture of DMSO and ethylacetate, isopropanol, a mixture of NMP and n-propanol, a mixture of methanol and water, a mixture of water, ethanol and acetone, NMP, 2-methyltetrahydrofuran, water, ethanol, methanol and mixtures thereof.

In another embodiment, the present invention encompasses a process for preparing crystalline sunitinib malate characterized by diffraction peaks at about 13.2 and 24.2 degrees two-theta comprising suspending a composition containing Sunitinib base and L-malic acid selected from a group consisting of: a composition containing Sunitinib base and L-malic acid characterized by data selected from the group consisting of: a PXRD pattern having any 5 peaks at positions selected from the group consisting of: 6.0, 7.7, 9.1, 10.1, 12.0, 14.5, 23.4 and 27.1±0.2 degrees 2-theta, and a PXRD pattern as depicted in FIG. 3; a composition containing Sunitinib base and L-malic acid characterized by data selected from the group consisting of: a PXRD pattern having any 5 peaks at positions selected from the group consisting of: 6.2, 7.7, 9.3, 12.4, 14.5, 23.2 and 27.4±0.2 degrees 2-theta, and a PXRD pattern as depicted in FIG. 4; a composition containing Sunitinib base and L-malic acid characterized by data selected from the group consisting of: a PXRD pattern having any 5 peaks at positions selected from the group consisting of: 6.0, 7.8, 9.0, 12.0, 14.8, 18.0, 22.5 and 27.1±0.2 degrees 2-theta, and a PXRD pattern as depicted in FIG. 5; a composition containing Sunitinib base and L-malic acid characterized by data selected from the group consisting of: a PXRD pattern having any 5 peaks at positions selected from the group consisting of: 6.0, 7.8, 9.0, 12.0, 14.8, 18.0, 22.5 and 27.1±0.2 degrees 2-theta, and a PXRD pattern as depicted in FIG. 5; a composition containing Sunitinib base and L-malic acid characterized by data selected from the group consisting of: a PXRD pattern having any 5 peaks at positions selected from the group consisting of: 6.0, 7.7, 9.2, 12.2, 14.5, 22.9 and 27.3±0.2 degrees 2-theta, and a PXRD pattern as depicted in FIG. 6; a composition containing Sunitinib base and L-malic acid characterized by data selected from the group consisting of: a PXRD pattern having any 5 peaks at positions selected from the group consisting of: 11.4, 14.4, 23.4, 24.1 and 27.0±0.2 degrees 2-theta, and a PXRD pattern as depicted in FIG. 7; a composition containing Sunitinib base and L-malic acid characterized by data selected from the group consisting of a PXRD pattern having any 5 peaks at positions selected from the group consisting of: 5.9, 8.9, 11.8, 20.6, 22.6 and 27.3±0.2 degrees 2-theta, and a PXRD pattern as depicted in FIG. 8; a composition containing Sunitinib base and L-malic acid characterized by data selected from the group consisting of: a PXRD pattern having any 5 peaks at positions selected from the group consisting of: 6.0, 7.4, 8.9, 11.9, 23.4 and 27.7±0.2 degrees 2-theta and a PXRD pattern as depicted in FIG. 10; and a composition containing Sunitinib base and L-malic acid characterized by data selected from the group consisting of: a PXRD pattern having any 5 peaks at positions selected from the group consisting of: 6.1, 7.9, 9.2, 12.1, 15.2, 22.9 and 27.7±0.2 degrees 2-theta and a PXRD pattern as depicted in FIG. 11; and mixtures thereof in either methanol, ethanol or water, wherein when the solvent is either methanol or ethanol the composition is selected from a group consisting of: a composition containing Sunitinib base and L-malic acid characterized by data selected from the group consisting of: a PXRD pattern having any 5 peaks at positions selected from the group consisting of: 6.0, 7.7, 9.1, 10.1, 12.0, 14.5, 23.4 and 27.1±0.2 degrees 2-theta, and a PXRD pattern as depicted in FIG. 3; a composition containing Sunitinib base and L-malic acid characterized by data selected from the group consisting of a PXRD pattern having any 5 peaks at positions selected from the group consisting of: 6.2, 7.7, 9.3, 12.4, 14.5, 23.2 and 27.4±0.2 degrees 2-theta, and a PXRD pattern as depicted in FIG. 4; a composition containing Sunitinib base and L-malic acid characterized by data selected from the group consisting of a PXRD pattern having any 5 peaks at positions selected from the group consisting of: 6.0, 7.8, 9.0, 12.0, 14.8, 18.0, 22.5 and 27.1±0.2 degrees 2-theta, and a PXRD pattern as depicted in FIG. 5; a composition containing Sunitinib base and L-malic acid characterized by data selected from the group consisting of a PXRD pattern having any 5 peaks at positions selected from the group consisting of: 6.0, 7.7, 9.2, 12.2, 14.5, 22.9 and 27.3±0.2 degrees 2-theta, and a PXRD pattern as depicted in FIG. 6; a composition containing Sunitinib base and L-malic acid characterized by data selected from the group consisting of a PXRD pattern having any 5 peaks at positions selected from the group consisting of: 11.4, 14.4, 23.4, 24.1 and 27.0±0.2 degrees 2-theta, and a PXRD pattern as depicted in FIG. 7; a composition containing Sunitinib base and L-malic acid characterized by data selected from the group consisting of: a PXRD pattern having any 5 peaks at positions selected from the group consisting of: 5.9, 8.9, 11.8, 20.6, 22.6 and 27.3±0.2 degrees 2-theta, and a PXRD pattern as depicted in FIG. 8; a composition containing Sunitinib base and L-malic acid characterized by data selected from the group consisting of a PXRD pattern having any 5 peaks at positions selected from the group consisting of: 6.0, 7.4, 8.9, 11.9, 23.4 and 27.7±0.2 degrees 2-theta and a PXRD pattern as depicted in FIG. 10; and a composition containing Sunitinib base and L-malic acid characterized by data selected from the group consisting of a PXRD pattern having any 5 peaks at positions selected from the group consisting of: 6.1, 7.9, 9.2, 12.1, 15.2, 22.9 and 27.7±0.2 degrees 2-theta and a PXRD pattern as depicted in FIG. 11; and mixtures thereof, and when the solvent is water the composition is selected from a group consisting of: a composition containing Sunitinib base and L-malic acid characterized by data selected from the group consisting of: a PXRD pattern having any 5 peaks at positions selected from the group consisting of: 6.0, 7.8, 9.0, 12.0, 14.8, 18.0, 22.5 and 27.1±0.2 degrees 2-theta, and a PXRD pattern as depicted in FIG. 5; a composition containing Sunitinib base and L-malic acid characterized by data selected from the group consisting of: a PXRD pattern having any 5 peaks at positions selected from the group consisting of: 6.0, 7.7, 9.2, 12.2, 14.5, 22.9 and 27.3±0.2 degrees 2-theta, and a PXRD pattern as depicted in FIG. 6; a composition containing Sunitinib base and L-malic acid characterized by data selected from the group consisting of: a PXRD pattern having any 5 peaks at positions selected from the group consisting of: 11.4, 14.4, 23.4, 24.1 and 27.0±0.2 degrees 2-theta, and a PXRD pattern as depicted in FIG. 7; and mixtures thereof.

DETAILED DESCRIPTION OF THE INVENTION

As used herein, the term "crystalline sunitinib malate form 1" refers to a crystalline form characterized by diffraction peaks at about 13.2 and 24.2 degrees two-theta, and more preferably, at about 13.2, 19.4, 24.2 and 25.5 degrees two-theta.

Figure 1:
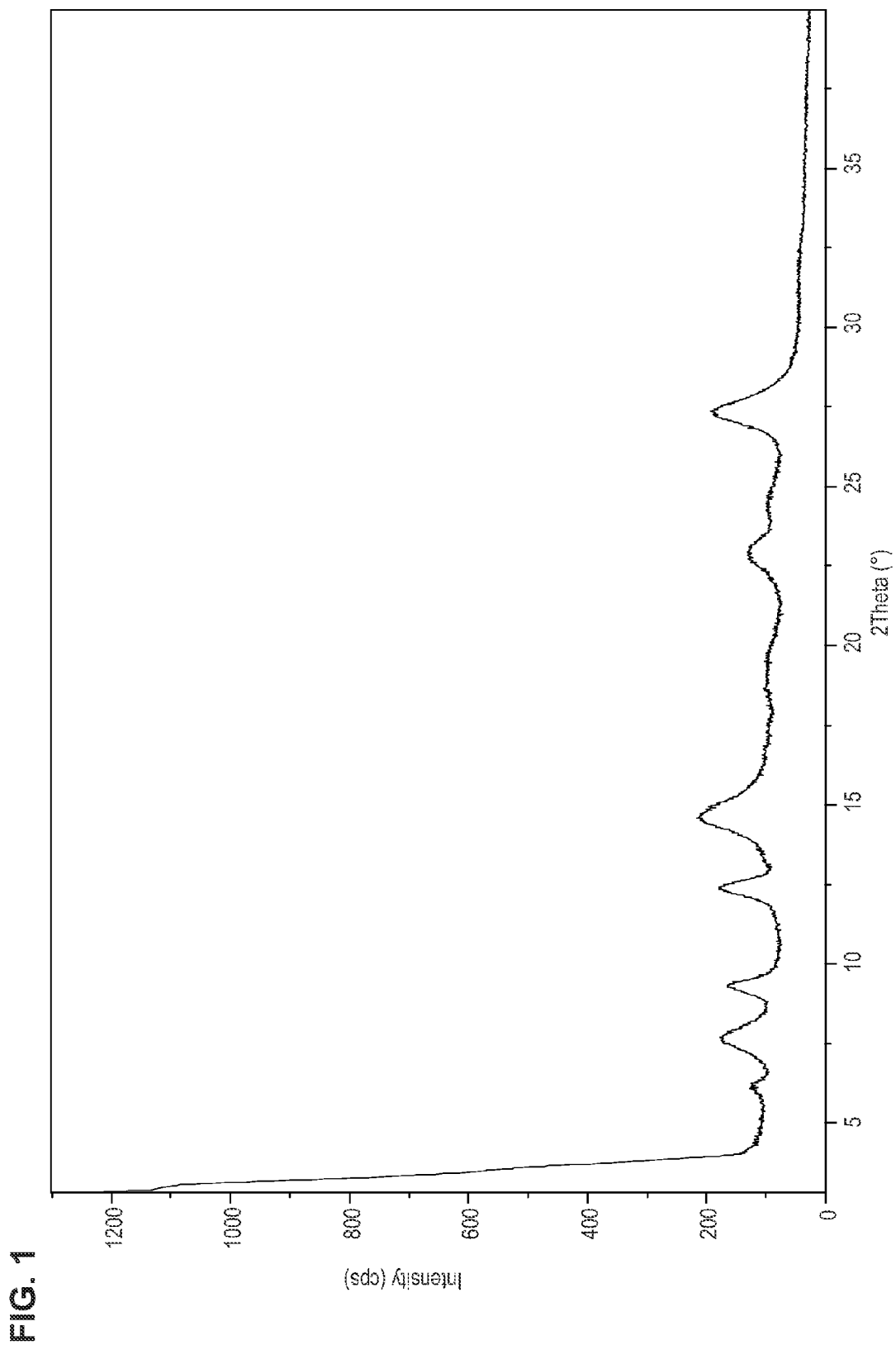
FIG. 1 shows a powder X-ray diffraction pattern of composition L containing Sunitinib base and L-malic acid.

As used herein, the term "composition L" refers to a composition containing Sunitinib base and L-malic acid characterized by data selected from the group consisting of: a PXRD pattern having any 5 peaks at positions selected from the group consisting of: 6.2, 7.6, 9.3, 12.4, 14.6, 22.9 and 27.4±0.2 degrees 2-theta, a PXRD pattern as depicted in FIG. 1, and combination thereof.

Figure 2:
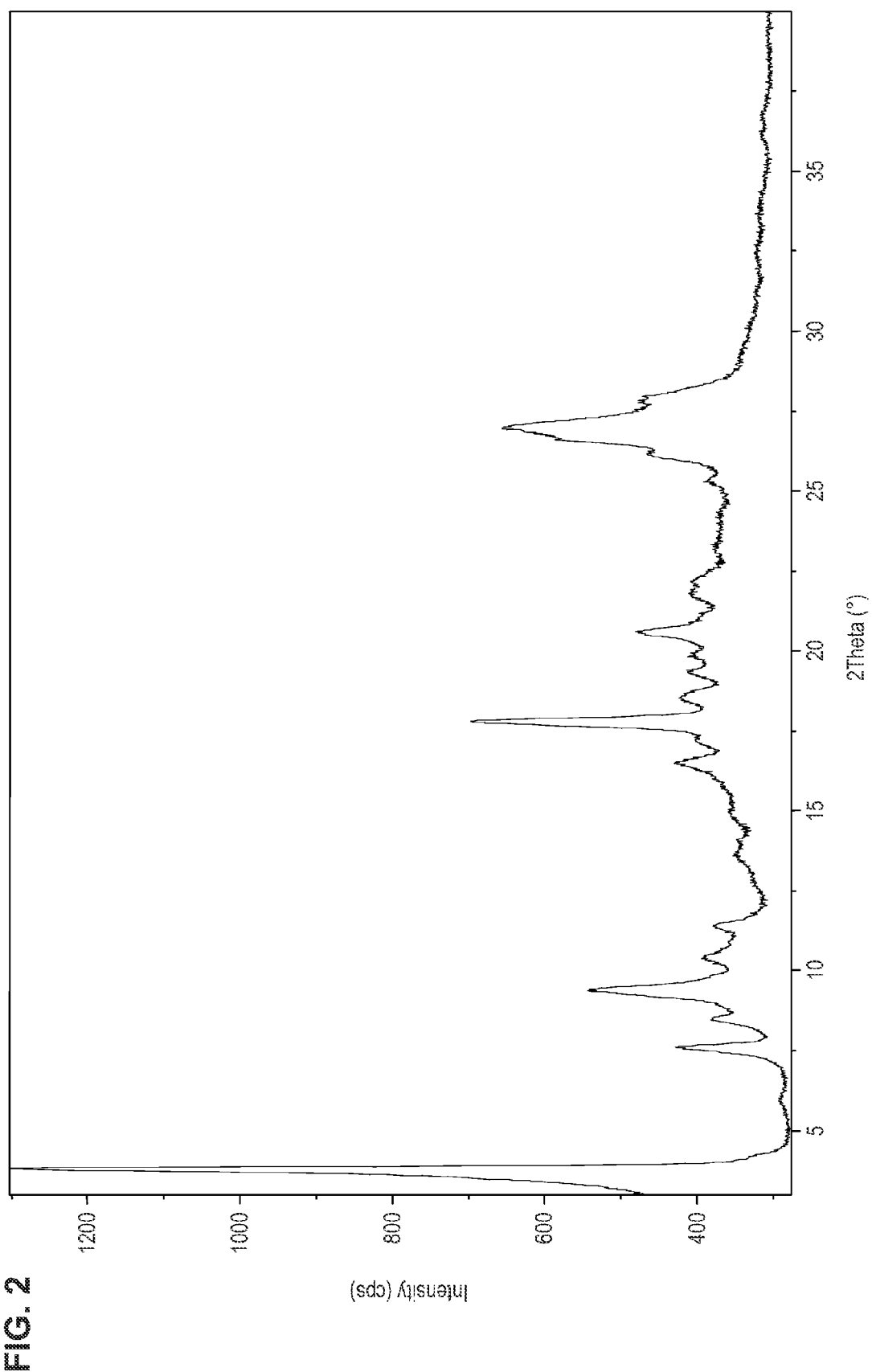
FIG. 2 shows a powder XRD pattern of crystalline Sunitinib base Form VIII.

As used herein, the term "crystalline sunitinib base form VIII" refers to crystalline sunitinib base characterized by data selected from a group consisting of: PXRD pattern having any 5 peaks selected from a list consisting of: 3.8, 7.6, 8.5, 9.5, 10.4, 11.4, 16.5, 17.8, 20.6, and 27.0 deg±0.2 degrees 2-theta and a PXRD pattern as depicted in FIG. 2.

Figure 3:
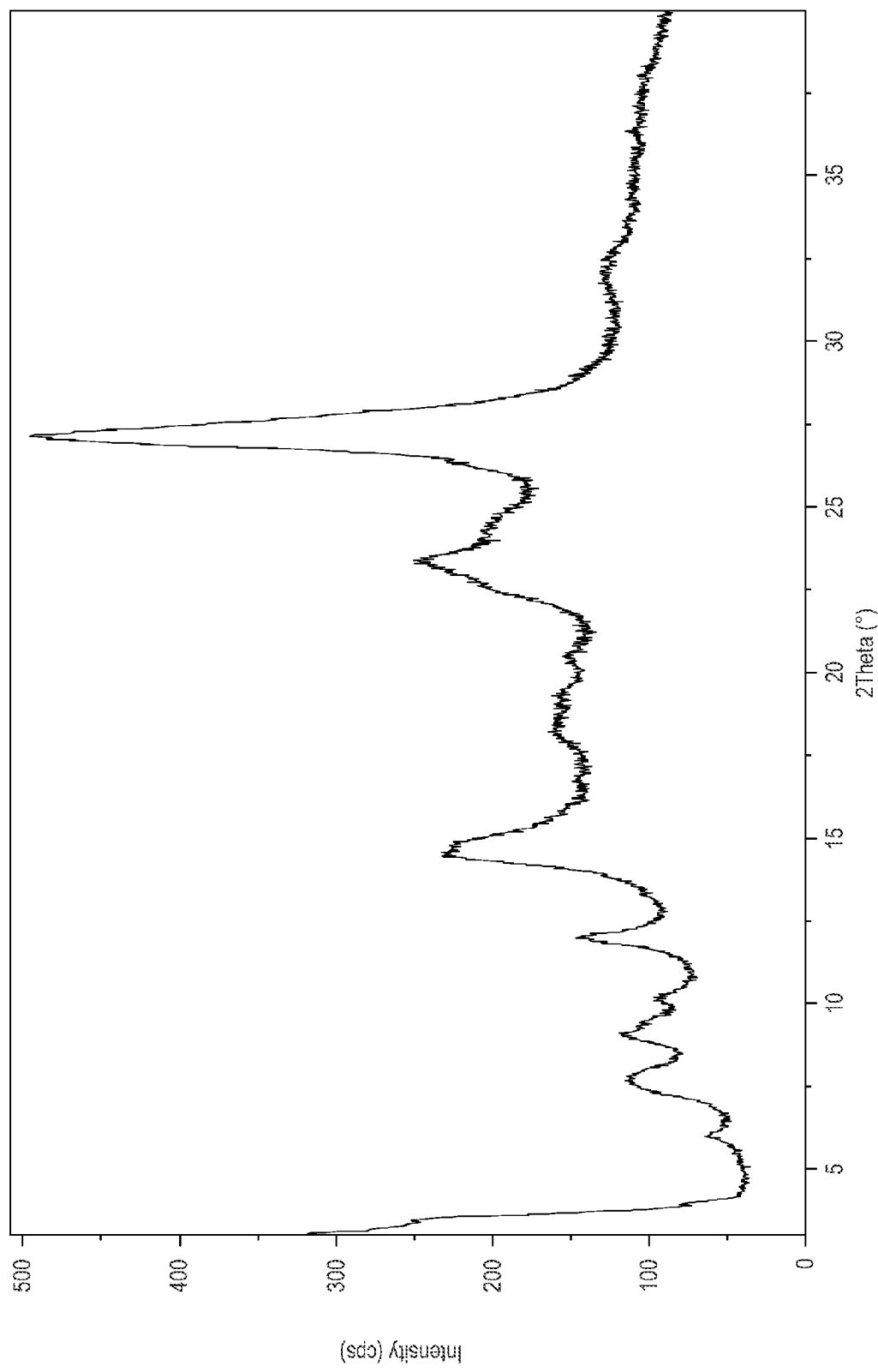
FIG. 3 shows a powder X-ray diffraction pattern of composition F containing Sunitinib base and L-malic acid.

As used herein, the term "composition F" refers to a composition containing Sunitinib base and L-malic acid characterized by data selected from the group consisting of: a PXRD pattern having any 5 peaks at positions selected from the group consisting of: 6.0, 7.7, 9.1, 10.1, 12.0, 14.5, 23.4 and 27.1±0.2 degrees 2-theta, and a PXRD pattern as depicted in FIG. 3.

Figure 4:
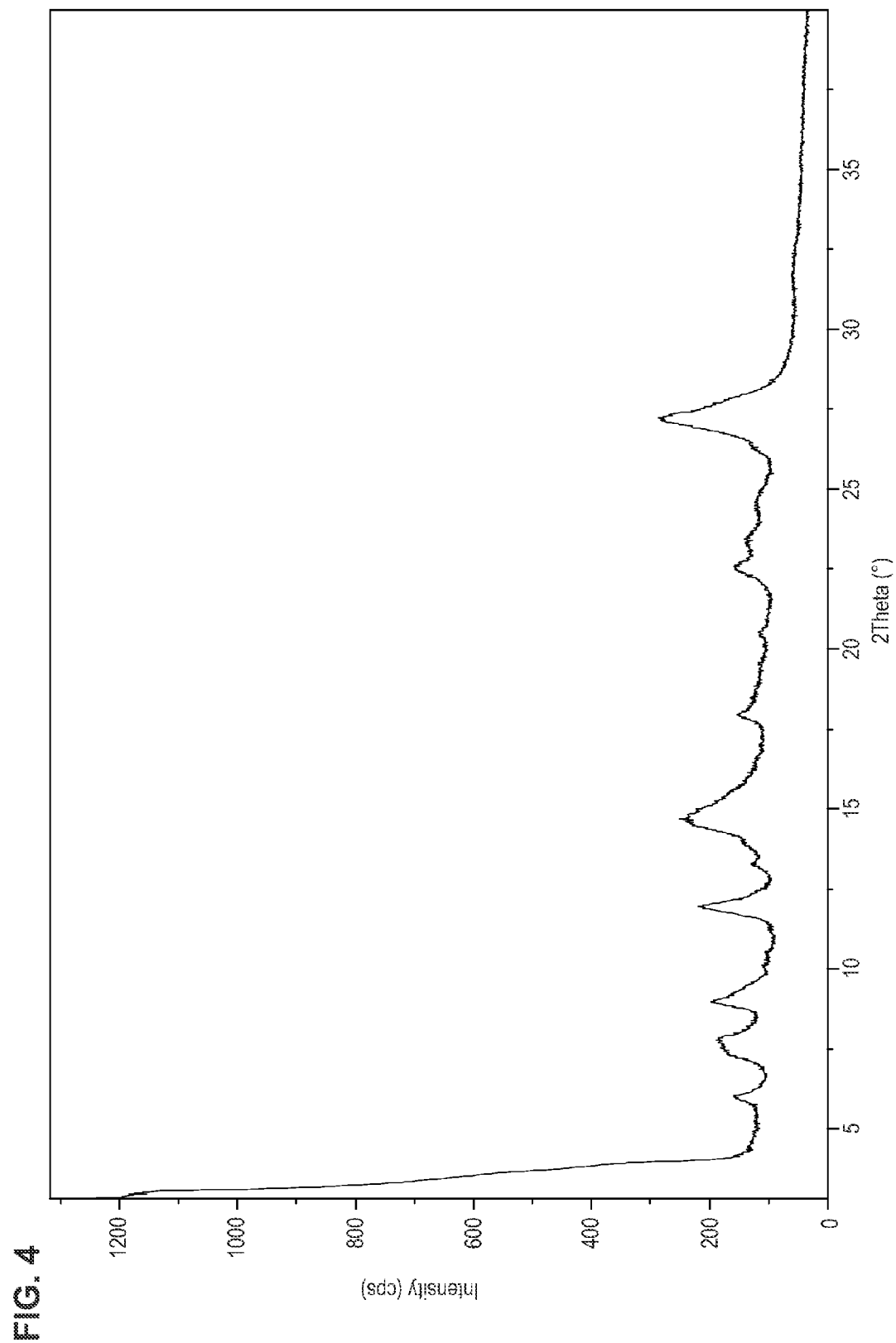
FIG. 4 shows a powder X-ray diffraction pattern of composition G containing Sunitinib base and L-malic acid.

As used herein, the term "composition G" refers to a composition containing Sunitinib base and L-malic acid characterized by data selected from the group consisting of: a PXRD pattern having any 5 peaks at positions selected from the group consisting of: 6.2, 7.7, 9.3, 12.4, 14.5, 23.2 and 27.4±0.2 degrees 2-theta, and a PXRD pattern as depicted in FIG. 4.

Figure 5:
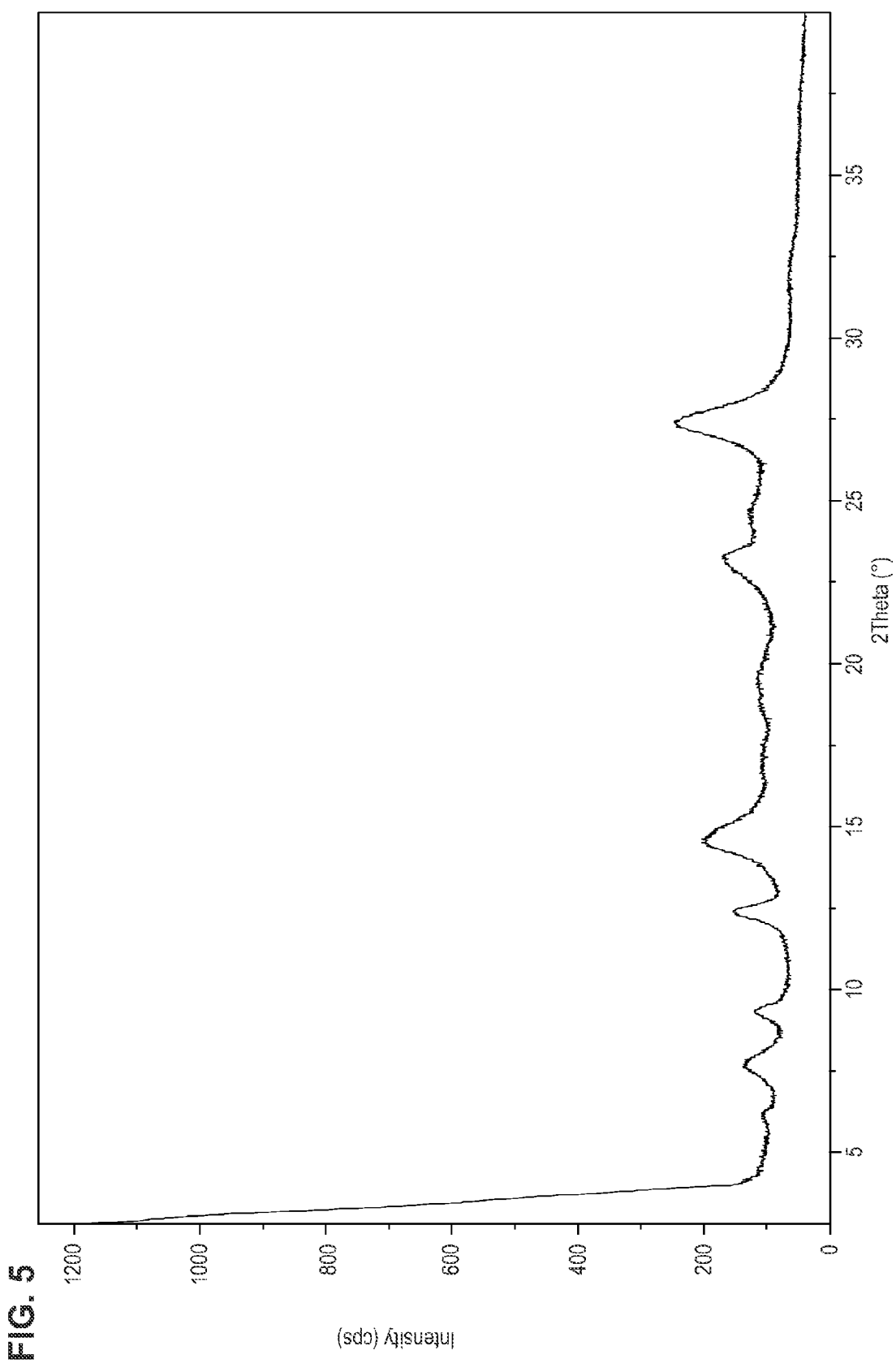
FIG. 5 shows a powder X-ray diffraction pattern of composition H containing Sunitinib base and L-malic acid.

As used herein, the term "composition H" refers to a composition containing Sunitinib base and L-malic acid characterized by data selected from the group consisting of: a PXRD pattern having any 5 peaks at positions selected from the group consisting of: 6.0, 7.8, 9.0, 12.0, 14.8, 18.0, 22.5 and 27.1±0.2 degrees 2-theta, and a PXRD pattern as depicted in FIG. 5.

Figure 6:
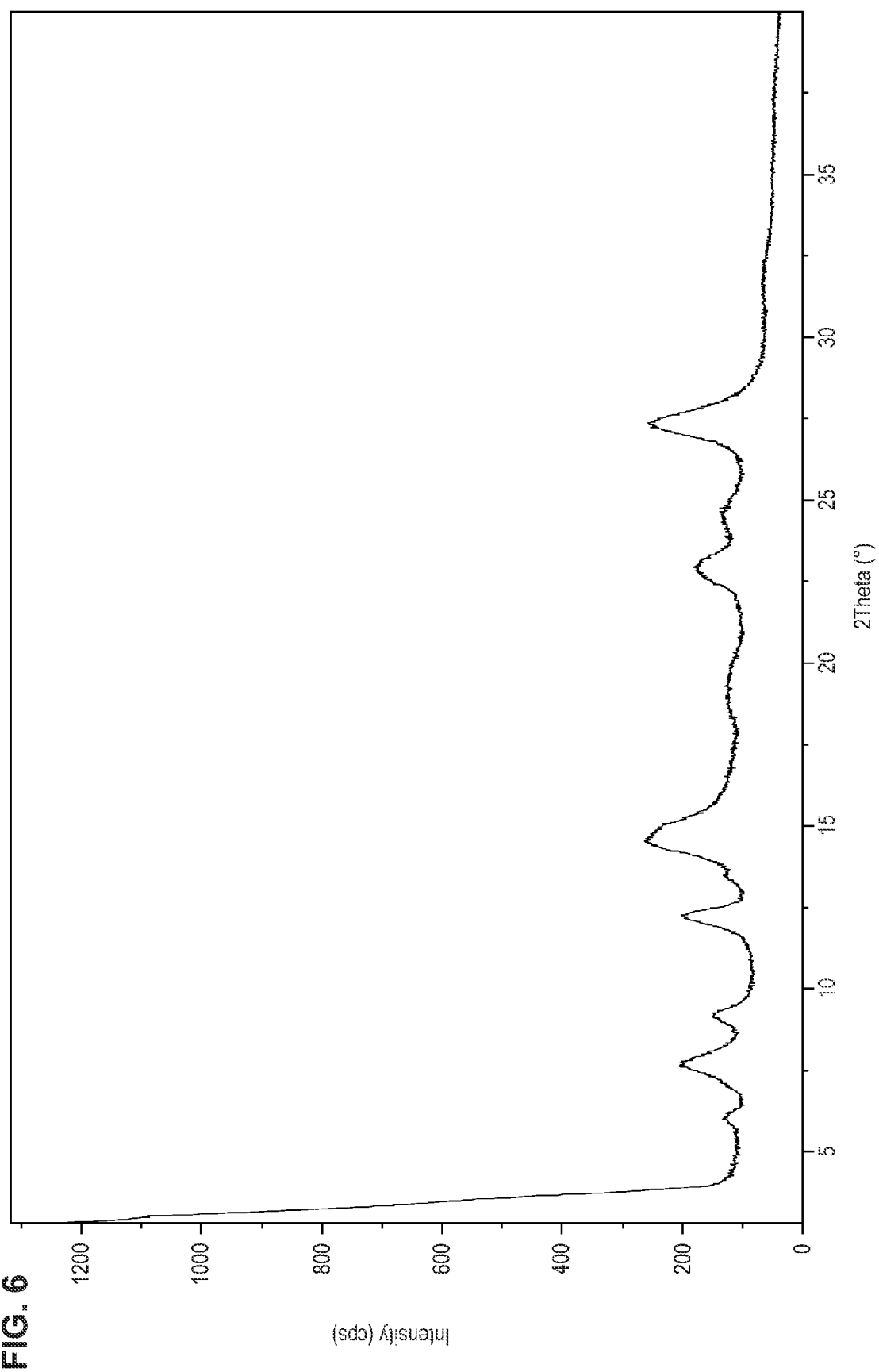
FIG. 6 shows a powder X-ray diffraction pattern of composition I containing Sunitinib base and L-malic acid.

As used herein, the term "composition I" refers to a composition containing Sunitinib base and L-malic acid characterized by data selected from the group consisting of: a PXRD pattern having any 5 peaks at positions selected from the group consisting of: 6.0, 7.7, 9.2, 12.2, 14.5, 22.9 and 27.3±0.2 degrees 2-theta, and a PXRD pattern as depicted in FIG. 6.

Figure 7:
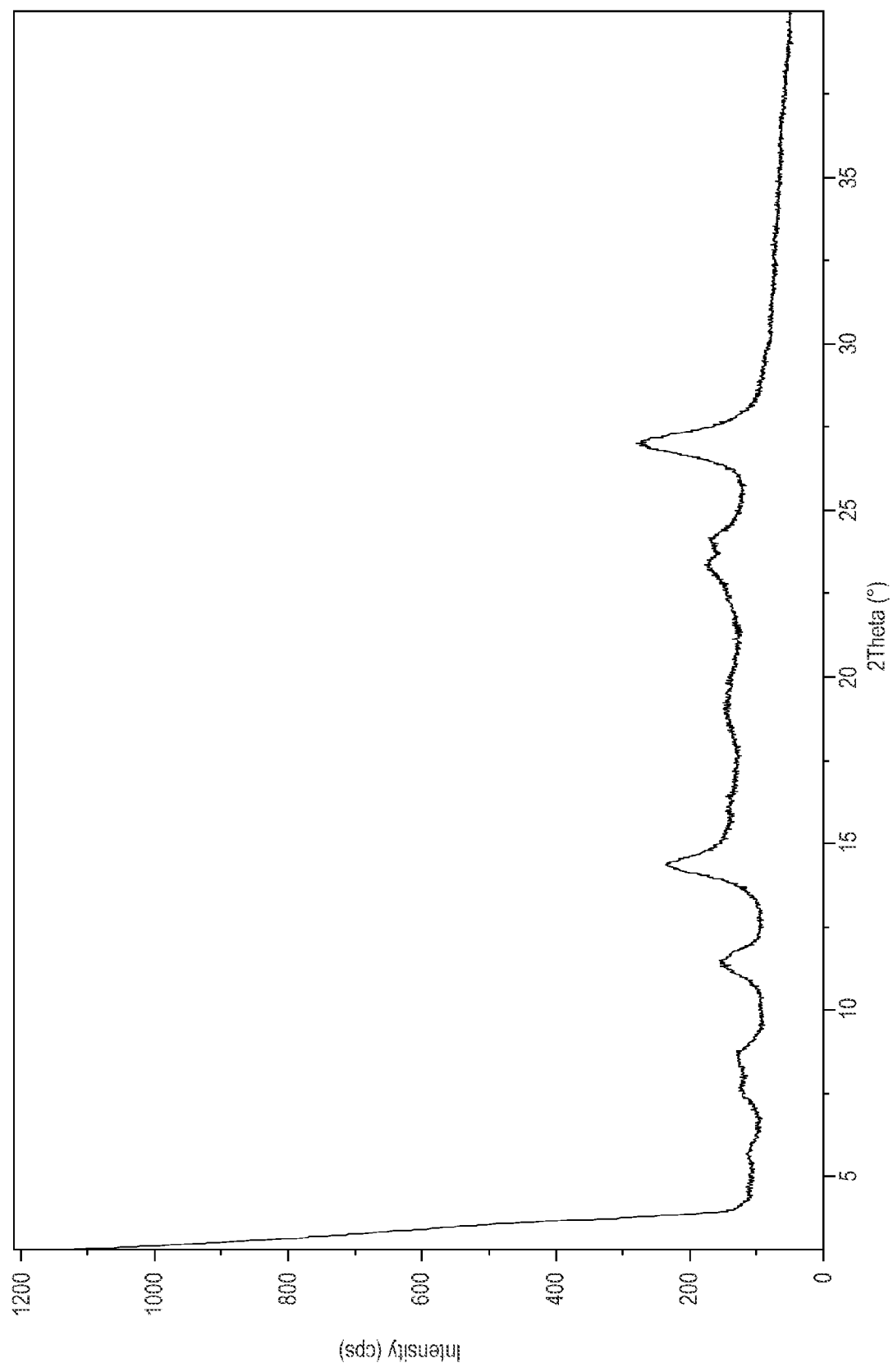
FIG. 7 shows a powder X-ray diffraction pattern of composition K containing Sunitinib base and L-malic acid.

As used herein, the term "composition K" refers to a composition containing Sunitinib base and L-malic acid characterized by data selected from the group consisting of: a PXRD pattern having any 5 peaks at positions selected from the group consisting of: 11.4, 14.4, 23.4, 24.1 and 27.0±0.2 degrees 2-theta, and a PXRD pattern as depicted in FIG. 7.

Figure 8:
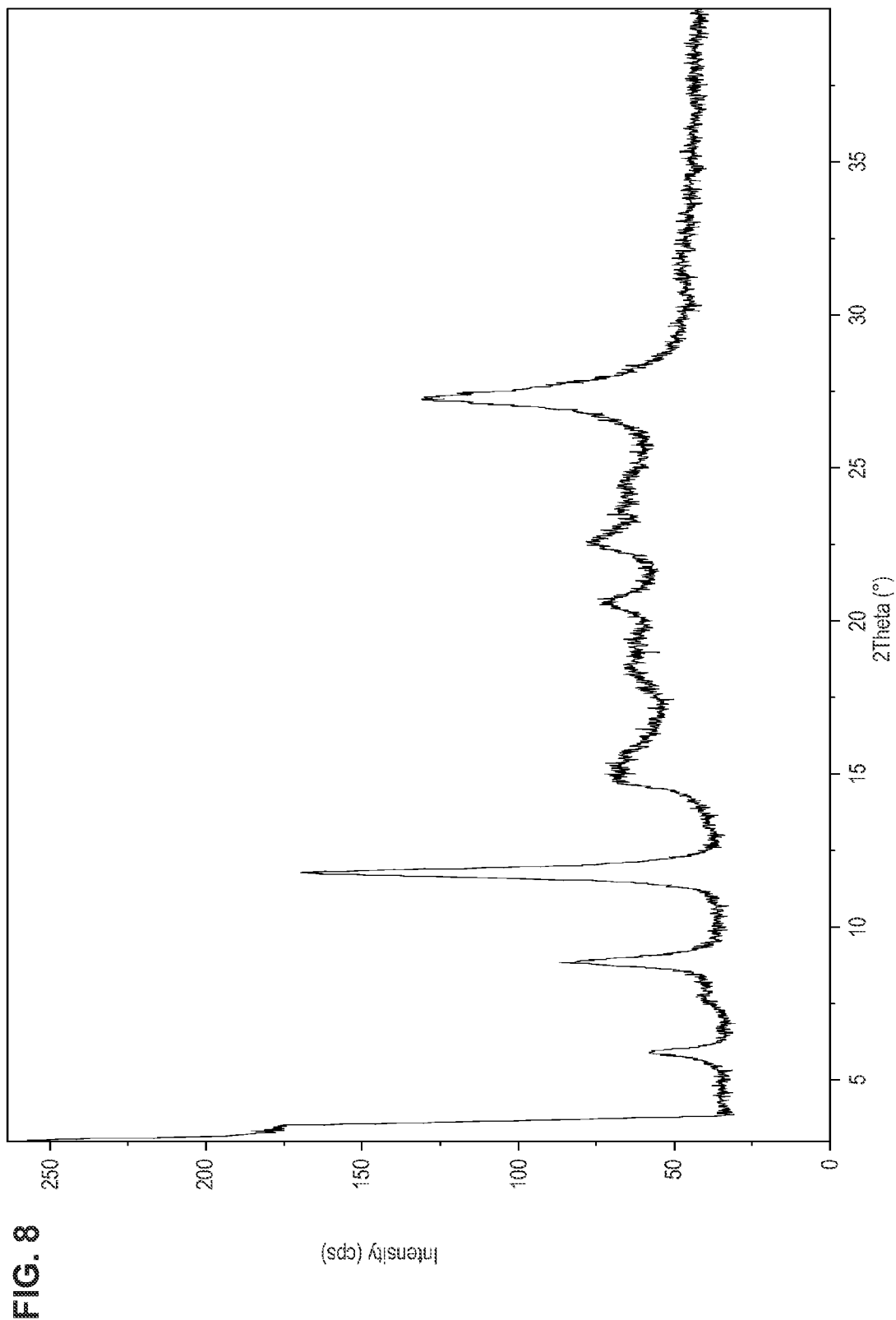
FIG. 8 shows a powder X-ray diffraction pattern of composition Q containing Sunitinib base and L-malic acid.
Figure 9:
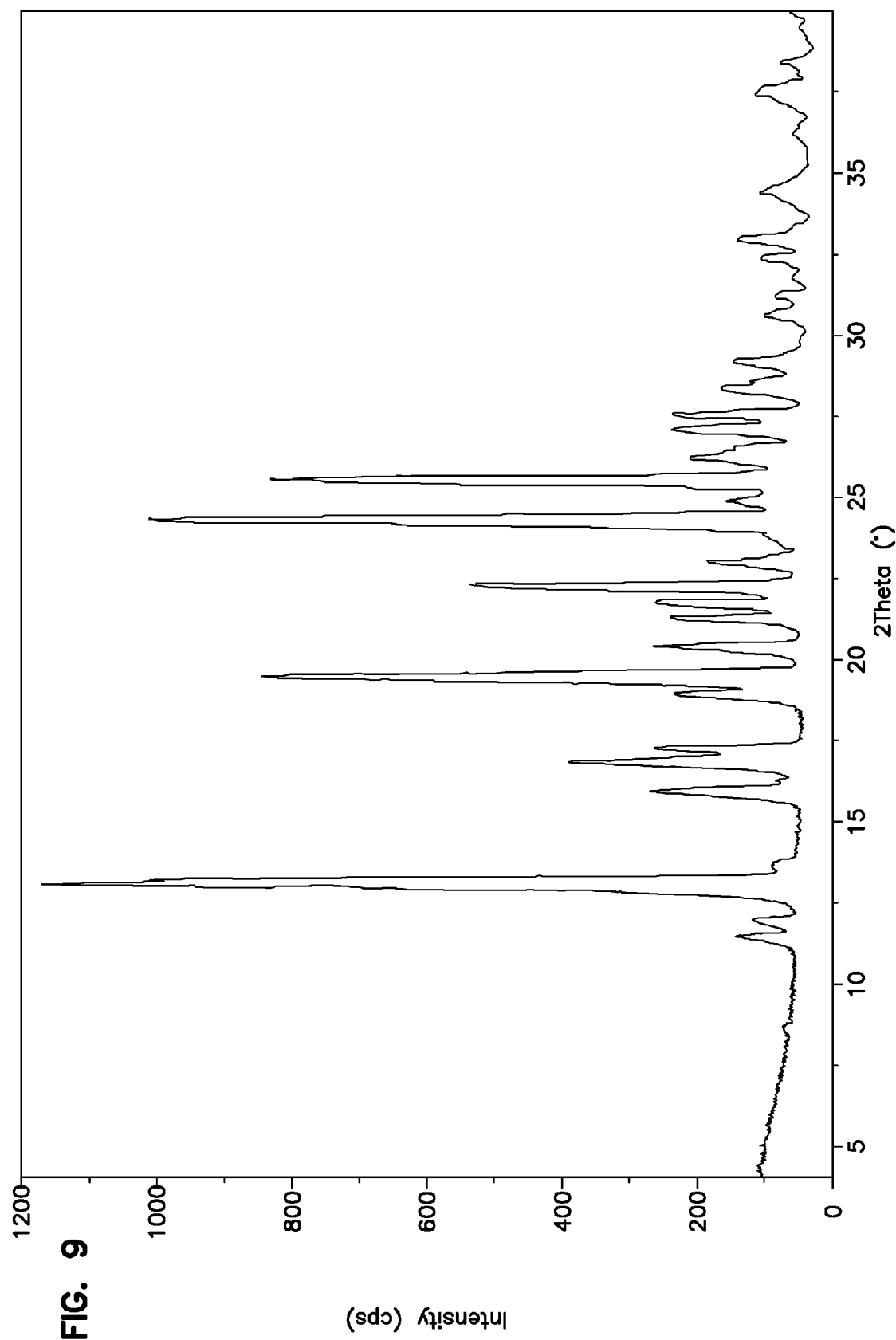
FIG. 9 shows a powder X-ray diffraction pattern of crystalline sunitinib malate form 1.

As used herein, the term "composition Q" refers to a composition containing Sunitinib base and L-malic acid characterized by data selected from the group consisting of: a PXRD pattern having any 5 peaks at positions selected from the group consisting of: 5.9, 8.9, 11.8, 20.6, 22.6 and 27.3±0.2 degrees 2-theta, and a PXRD pattern as depicted in FIG. 8.

Figure 10:
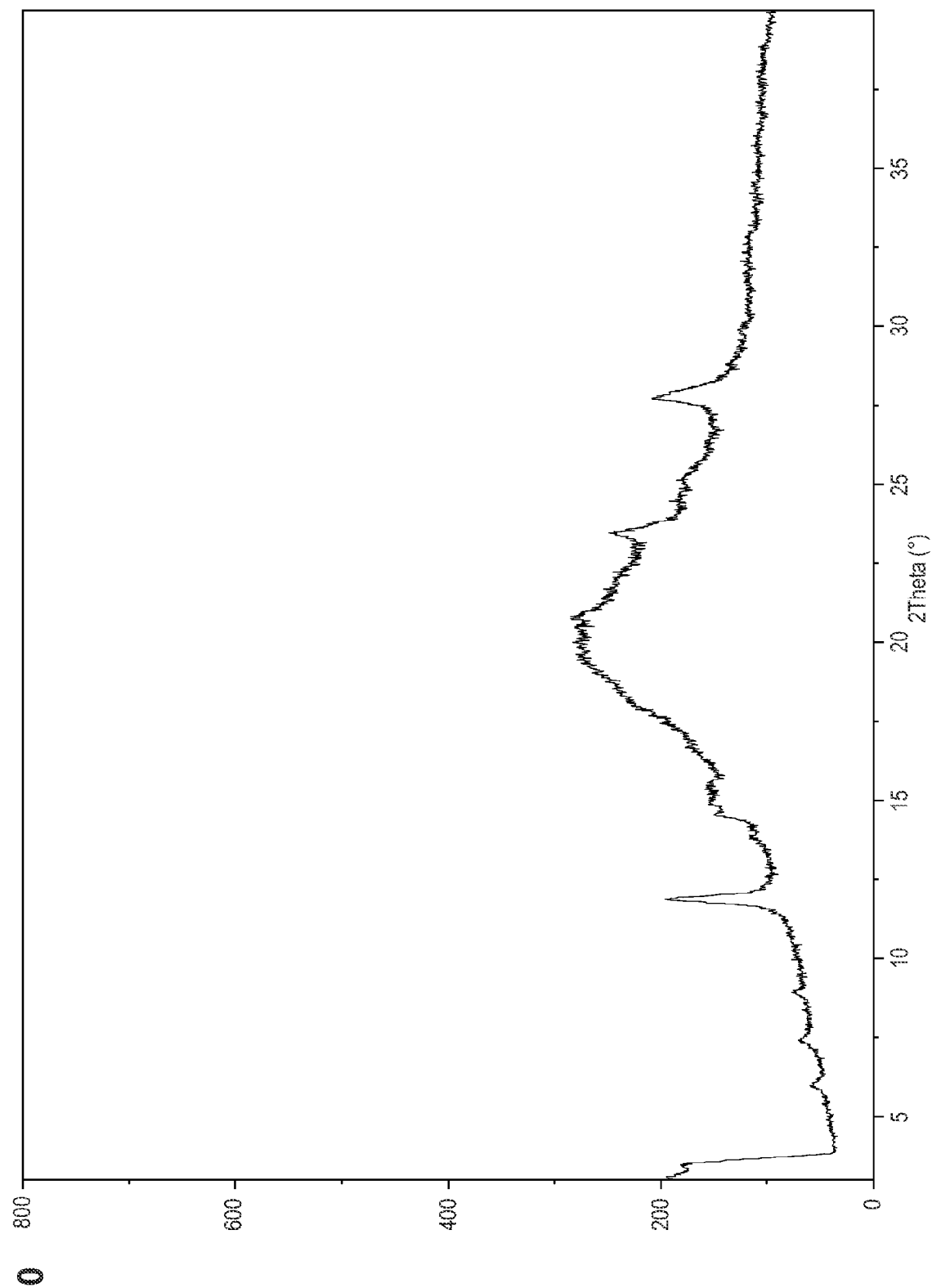
FIG. 10 shows a powder X-ray diffraction pattern of composition O containing Sunitinib base and L-malic acid.

As used herein, the term "composition O" refers to a composition containing Sunitinib base and L-malic acid characterized by data selected from the group consisting of: a PXRD pattern having any 5 peaks at positions selected from the group consisting of: 6.0, 7.4, 8.9, 11.9, 23.4 and 27.7±0.2 degrees 2-theta and a PXRD pattern as depicted in FIG. 10

Figure 11:
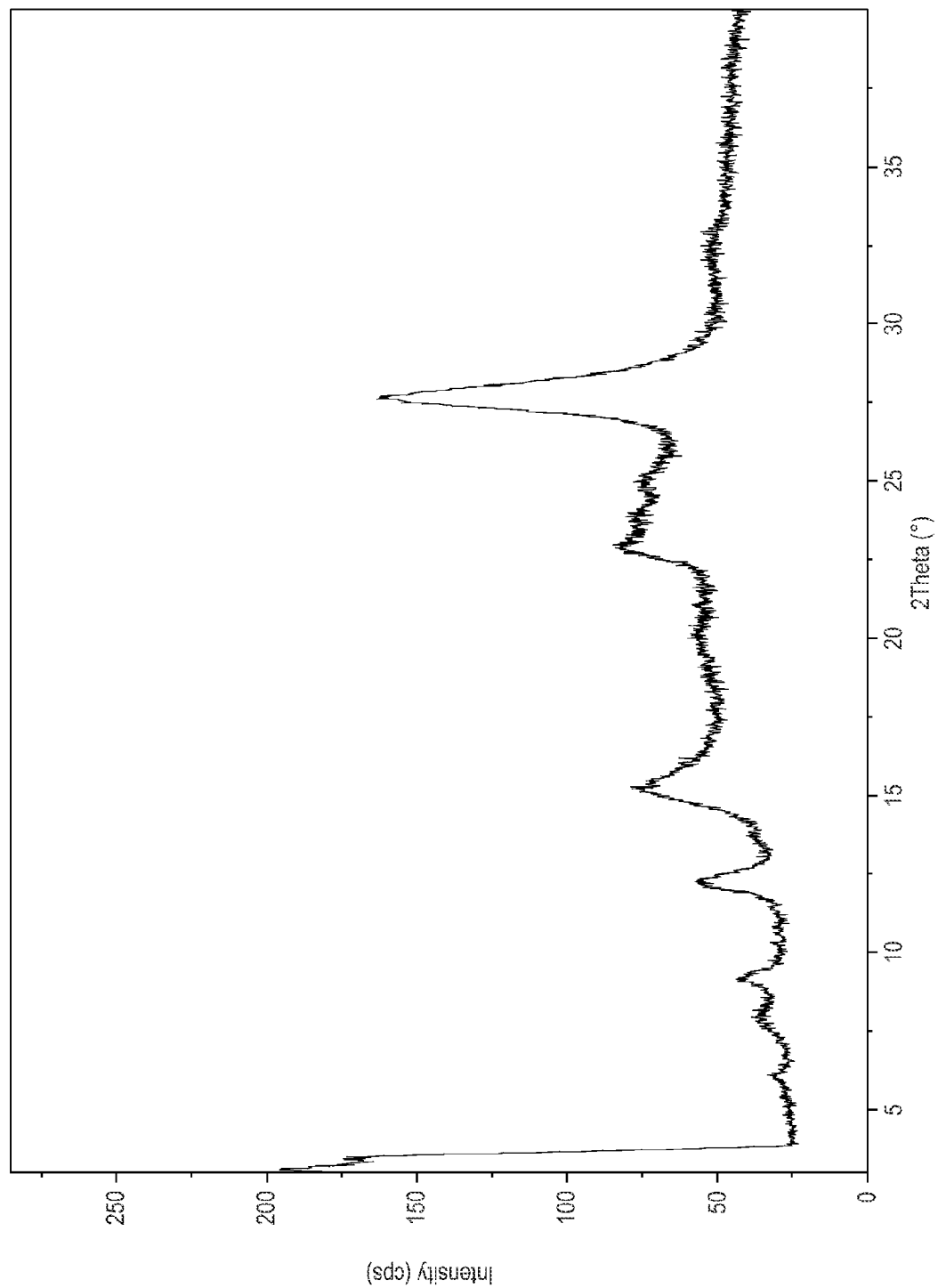
FIG. 11 shows a powder X-ray diffraction pattern of composition P containing Sunitinib base and L-malic acid.

As used herein, the term "composition P" refers to a composition containing Sunitinib base and L-malic acid characterized by data selected from the group consisting of: a PXRD pattern having any 5 peaks at positions selected from the group consisting of: 6.1, 7.9, 9.2, 12.1, 15.2, 22.9 and 27.7±0.2 degrees 2-theta and a PXRD pattern as depicted in FIG. 11.

As used herein, the terms "room temperature" or "ambient temperature" refers to a temperature of about 15° C. to about 30° C., more preferably, to a temperature of about 20° C. to about 25° C.

The present invention offers a new salt of Sunitinib, Sunitinib acetate, which can be used a useful intermediate for the preparation of Sunitinib malate; processes for preparation thereof; and its conversion to crystalline Sunitinib malate form 1.

The applicant has found that the preparation of Sunitinib malate via Sunitinib acetate is advantageous because Sunitinib acetate is soluble and can be made in situ for conversion to Sunitinib malate even without isolation. Further, Sunitinib acetate can be isolated as a crystalline solid, which is advantageous since this generally facilitates purification, isolation and handling.

The first process provided by the present invention yield Sunitinib malate via other addition salts, such as Sunitinib acetate, without conducting an isolation of these salts.

In one embodiment, Sunitinib malate form 1 can be prepared by a process comprising reacting Sunitinib base, a weak acid and L-malic acid in alcohol or a mixture of water and alcohol, and precipitating the said crystalline form 1 of Sunitinib malate.

As used herein, the term "weak acid" refers to acids having a pKa of about 3.40 to about 9.50, preferably, of about 3.40 to about 6.00, more preferably, of about 3.40.

Typically, the reaction between Sunitinib base and the weak acid provide an acid addition salt of sunitinib. Preferably, Sunitinib base, the weak acid and either alcohol or a mixture of water and alcohol are combined to obtain a first solution which is preferably heated.

Preferably, the heating is to a temperature of about 40° C. to about 60° C.

Preferably, the weak acid is selected from a group consisting of acetic acid, formic acid, ascorbic acid, benzoic acid, succinic acid, n-butyric acid, proionic acid and boric acid. More preferably, the weak acid is either acetic acid or formic acid. Most preferably, the weak acid is acetic acid.

Preferably, the acid addition salt of Sunitinib is either Sunitinib acetate or Sunitinib formate.

Preferably, the said alcohol is selected form a group consisting of methanol, ethanol and isopropanol, more preferably, ethanol.

Typically, the acid addition salt is soluble in the above solvents and also in other solvents that can be considered by one skilled in the art. If desired, the acid addition salt can be recovered from the solution, for example by precipitation and filtration. The isolated acid addition salt can then be dissolved in the above solvents before combining it with L-malic acid.

Further, the first solution is then preferably combined with L-malic acid to obtain a second solution.

Preferably, the second solution is provided either by addition of the first solution to a solution of L-malic acid in an alcohol, or the opposite.

Preferably, the addition is done at a temperature of about 40° C. to about 70° C., more preferably, at a temperature of about 55° C. to about 65° C., most preferably, at a temperature of about 60° C.

Precipitation can be performed by maintaining the said solution for about 10 to about 30 minutes, more preferably, for about 10 to about 15 minutes. Preferably, the solution is maintained at a temperature of about 60° C. Typically, precipitation forms a suspension.

Preferably, the obtained suspension can be further cooled after precipitation to a temperature of about 10° C. to about 0° C., more preferably, to a temperature of about 5° C. to about 0° C., most preferably, to a temperature of about 0° C.

Preferably, cooling is done for a period of about 1 hour to about 6 hours, more preferably, for about 1.5 hours to about 2.5 hours, most preferably, for about 2 hours.

Further, the cooled suspension can be further maintained at such temperature, prior to recovering the said crystalline form. Preferably, it is maintained from about 0.5 hour to about 5 hours, more preferably, for about 1 hour to about 3 hours, most preferably, for about 1 hour.

The process of preparing the said crystalline sunitinib malate form 1 may further comprise recovering the said crystalline form from the suspension. The recovery may be done for example, by filtering the suspension, washing the precipitate and drying.

Preferably, washing is done with ethanol. Typically, drying is done in oven under vacuum, preferably, at a temperature of about 45° C. to about 80° C., more preferably, to about 50° C. Preferably, drying is done for a period of about 1 hour to about 24 hours, more preferably, for about 16 to about 18 hours, most preferably, for about 18 hours. As mentioned before, a new salt of Sunitinib is also provided.

In one embodiment, the present invention encompasses Sunitinib acetate.

In a preferred embodiment, Sunitinib acetate is provided in an isolated form. Preferably, the isolated Sunitinib acetate is solid, more preferably, it is crystalline. As used herein, the term "isolated" in reference to Sunitinib acetate corresponds to Sunitinib acetate that is physically separated from the reaction mixture where it is formed.

Reported herein are two crystalline forms of Sunitinib acetate.

Figure 12:
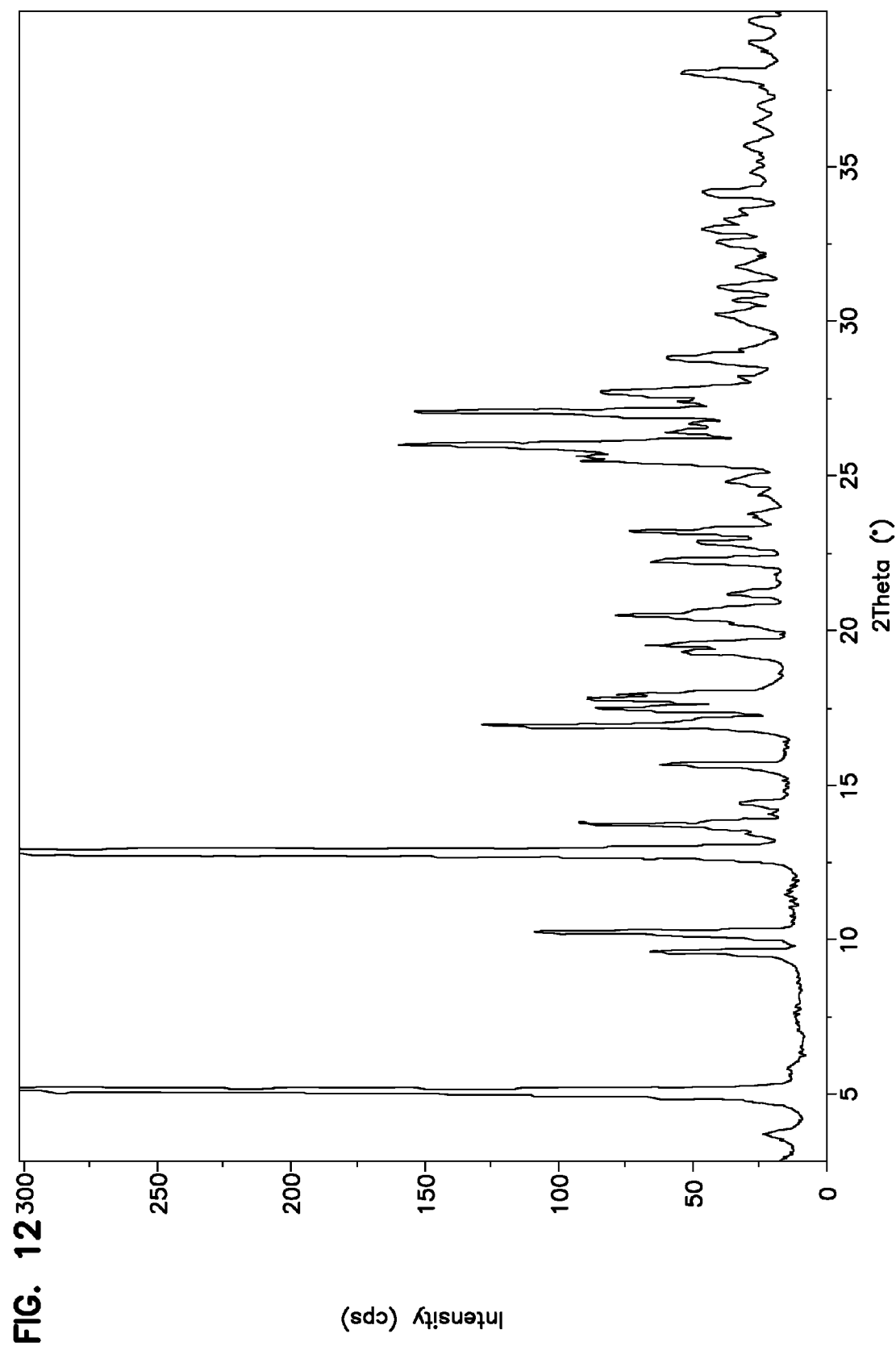
FIG. 12 shows a powder X-ray diffraction pattern of crystalline sunitinib acetate form Alpha.
Figure 20:
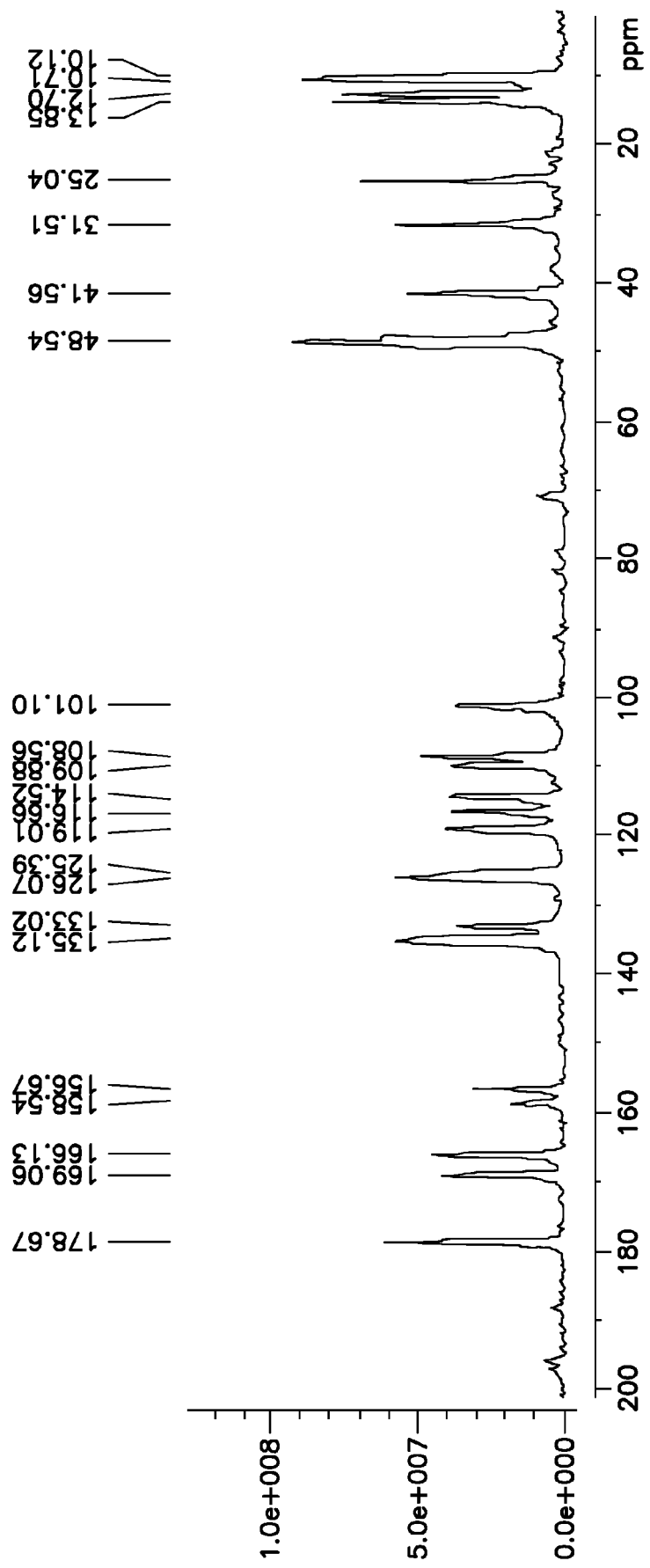
FIG. 20 shows a full-width solid state $^{13}C$ NMR spectrum of crystalline sunitinib acetate form Beta.

The first crystalline form of Sunitinib acetate is characterized by data selected from a group consisting of a PXRD pattern having peaks at about 5.1, 9.6, 10.2, 12.8 and 16.9±0.2 degrees 2-theta, a PXRD pattern as depicted in FIG. 12, a solid-state $^{13}$C NMR spectrum having signals at about 165.2, 134.5, 130.4, 118.7, 115.7, 112.5 and 110.9±0.2 ppm, a solid-state $^{13}$C NMR spectrum having chemical shifts differences between the signal exhibiting the lowest chemical shift and another in the chemical shift range of 100 to 180 ppm of about 63.6, 32.9, 28.8, 17.1, 14.1, 10.8 and 9.2±0.1 ppm, a solid-state $^{13}$C NMR spectrum depicted in FIG. 20 and a combination thereof. This form can be designated as form Alpha.

Typically, the signal exhibiting the lowest chemical shift in the chemical shift area of 100 to 180 ppm is at about 101.6±1.0 ppm.

Figure 13:
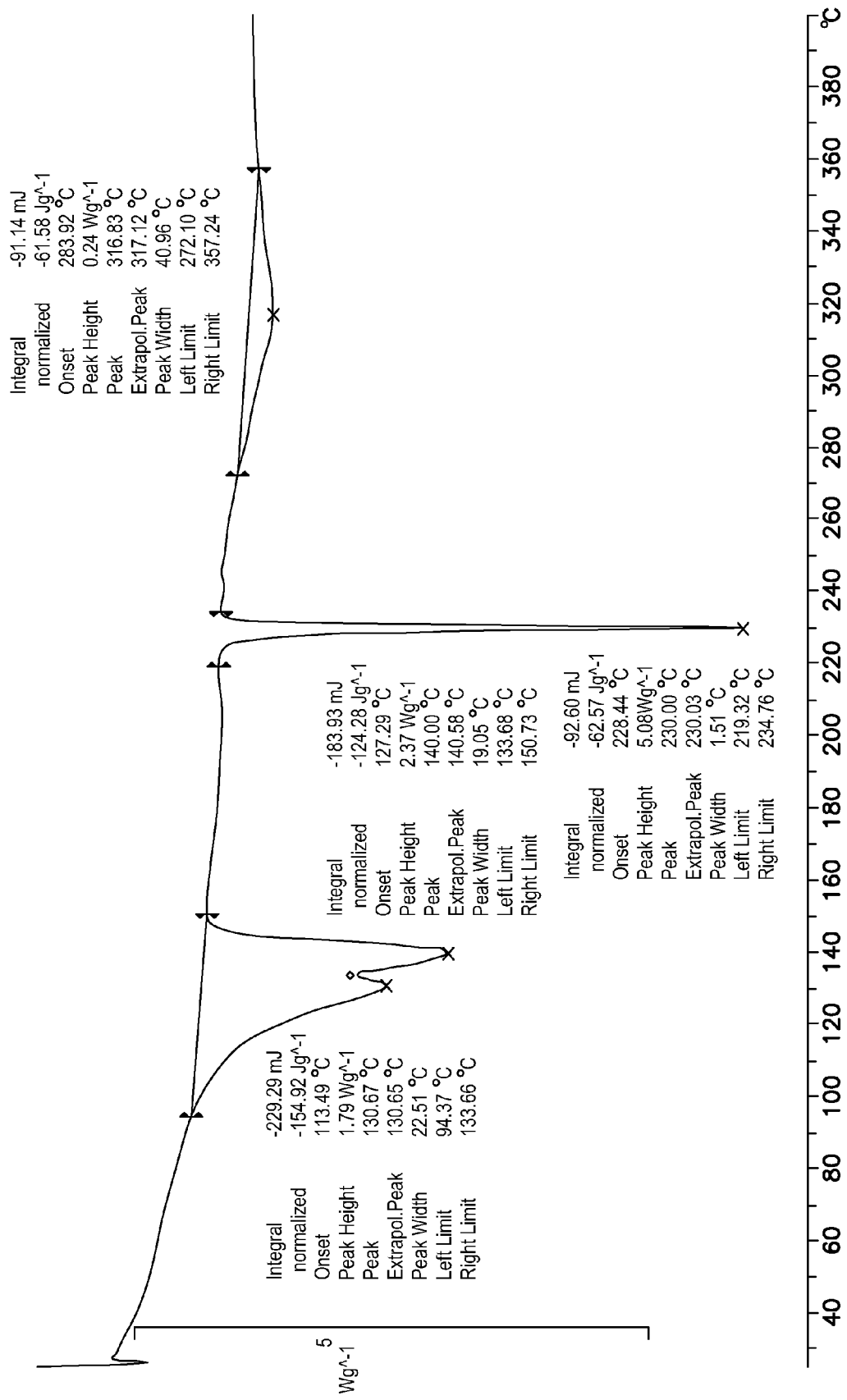
FIG. 13 shows a DSC thermogram of crystalline sunitinib acetate form Alpha.
Figure 14:
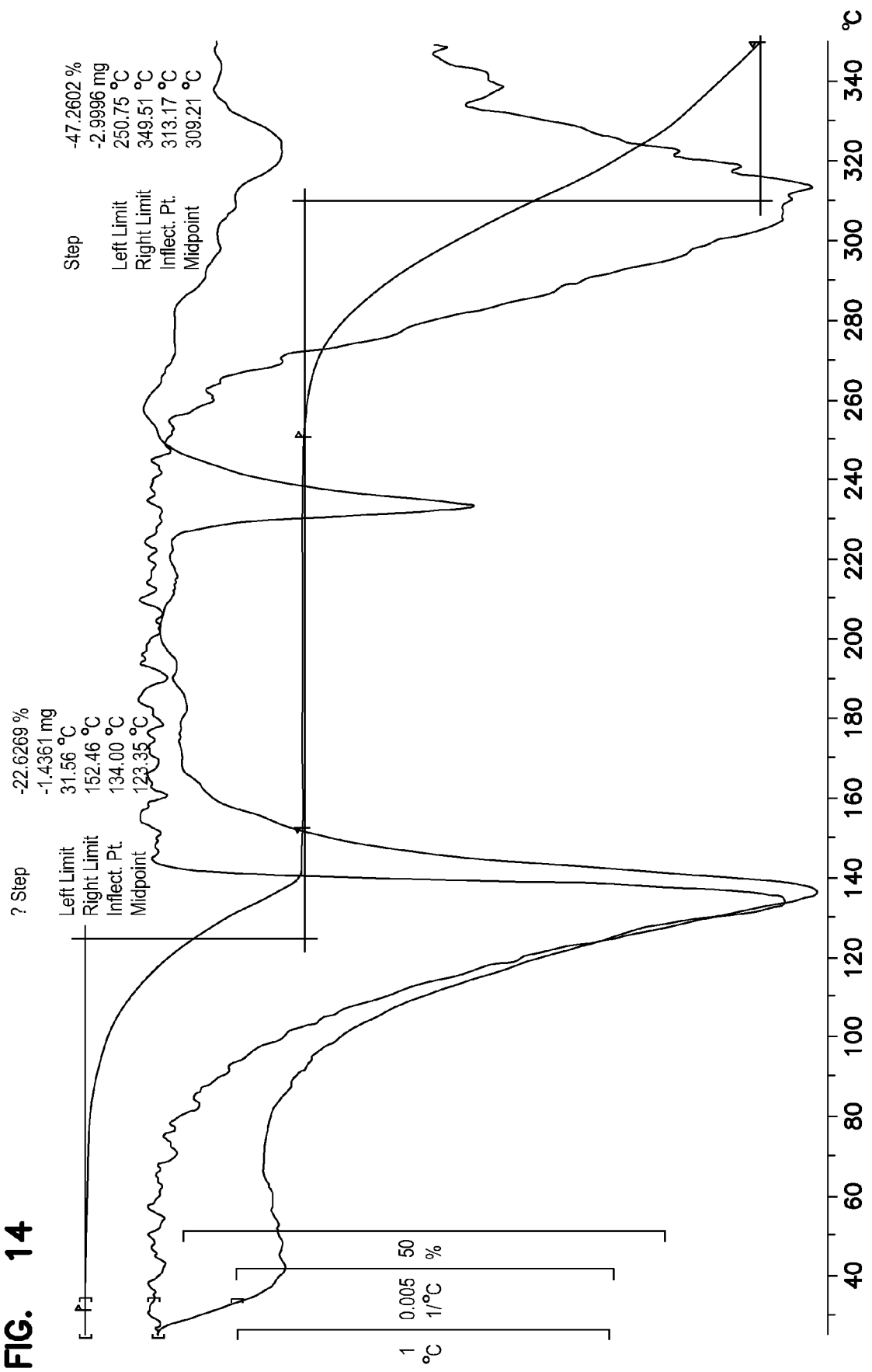
FIG. 14 shows a TGA thermogram of crystalline sunitinib acetate form Alpha.
Figure 15:
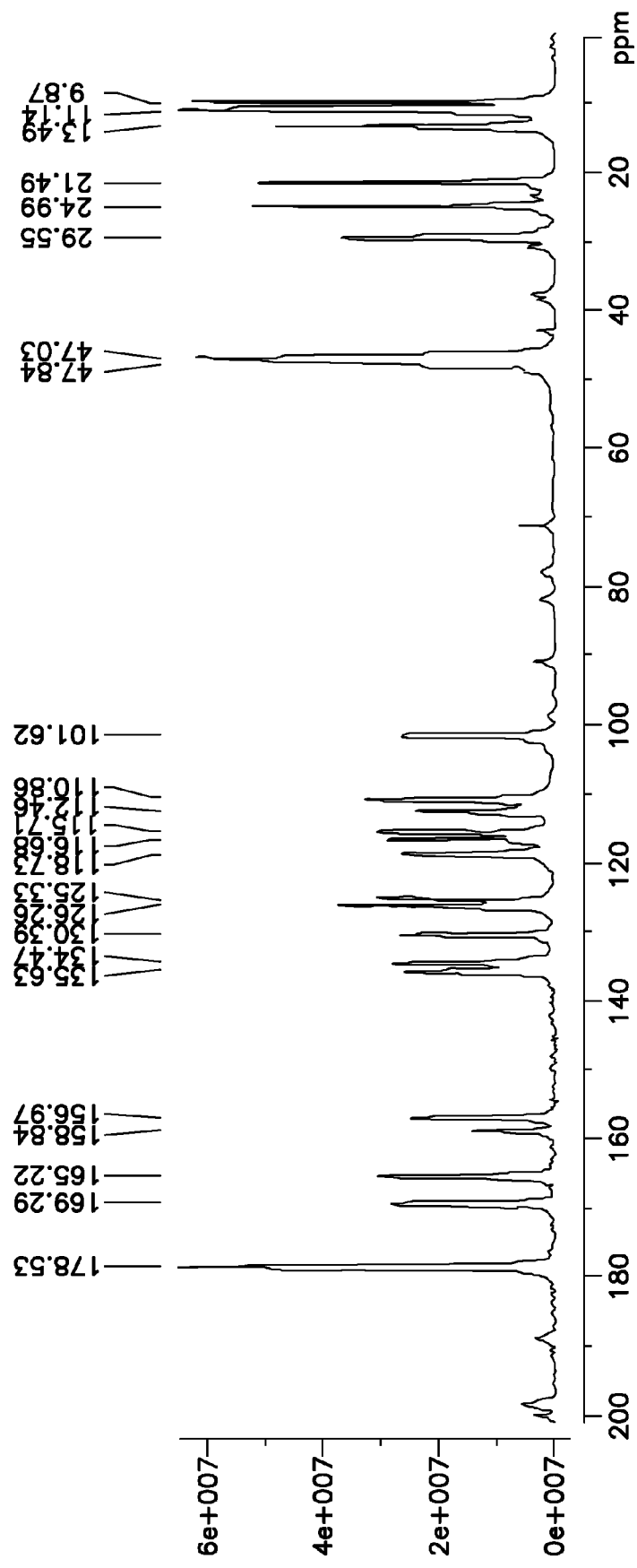
FIG. 15 shows a full-width solid state $^{13}C$ NMR spectrum of crystalline sunitinib acetate form Alpha.
Figure 16:
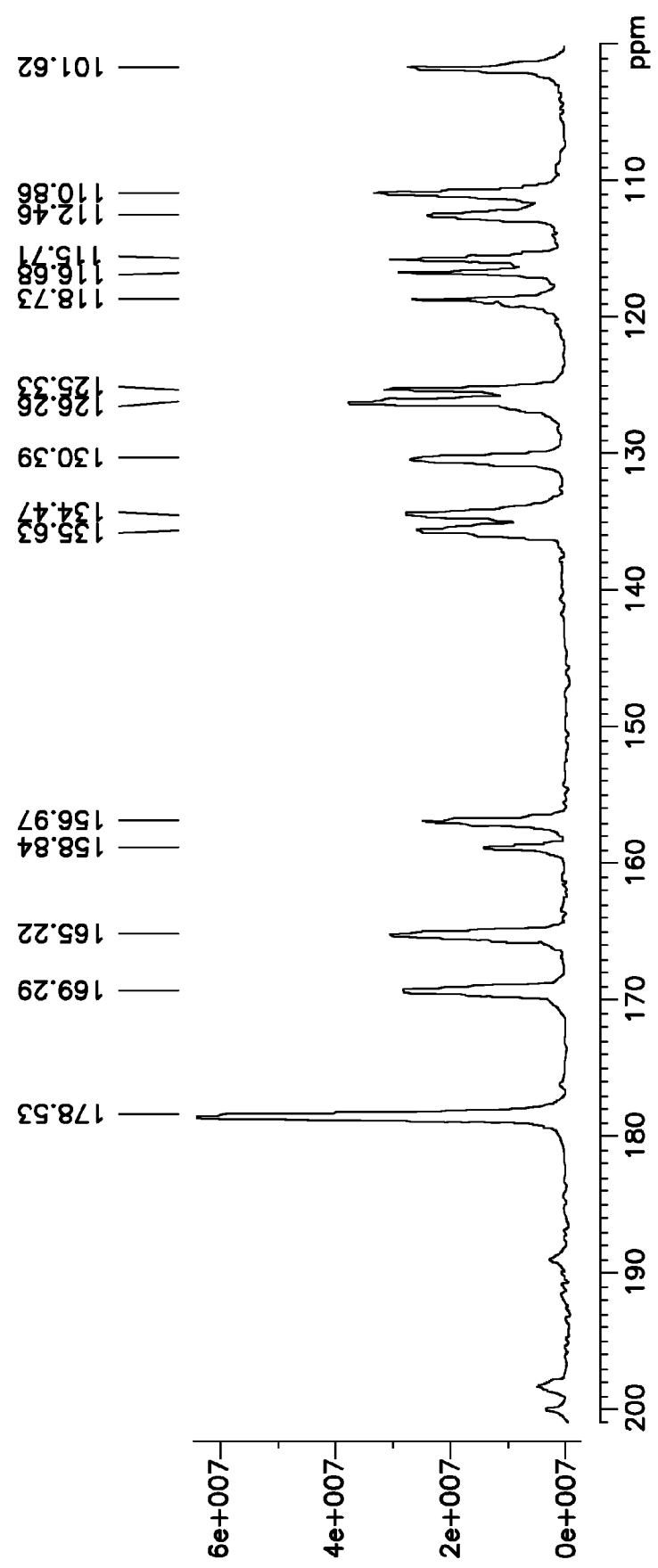
FIG. 16 shows a detailed solid state $^{13}C$ NMR spectrum of crystalline sunitinib acetate form Alpha.

Sunitinib acetate form Alpha can be further characterized by data selected from a group consisting of: a PXRD pattern having peaks at about 17.4, 17.7, 23.1, 26.0 and 27.0±0.2 degrees 2-theta, a DSC thermogram as depicted in FIG. 13 and a TGA thermogram as depicted in FIG. 14.

Crystalline Sunitinib acetate form Alpha is an acetic acid solvate of Sunitinib acetate. Preferably, the amount of acetic acid as measured by TGA is of about 20% to about 26% by weight, more preferably, of about 22% to 24% by weight, most preferably, of about 23% by weight.

Figure 17:
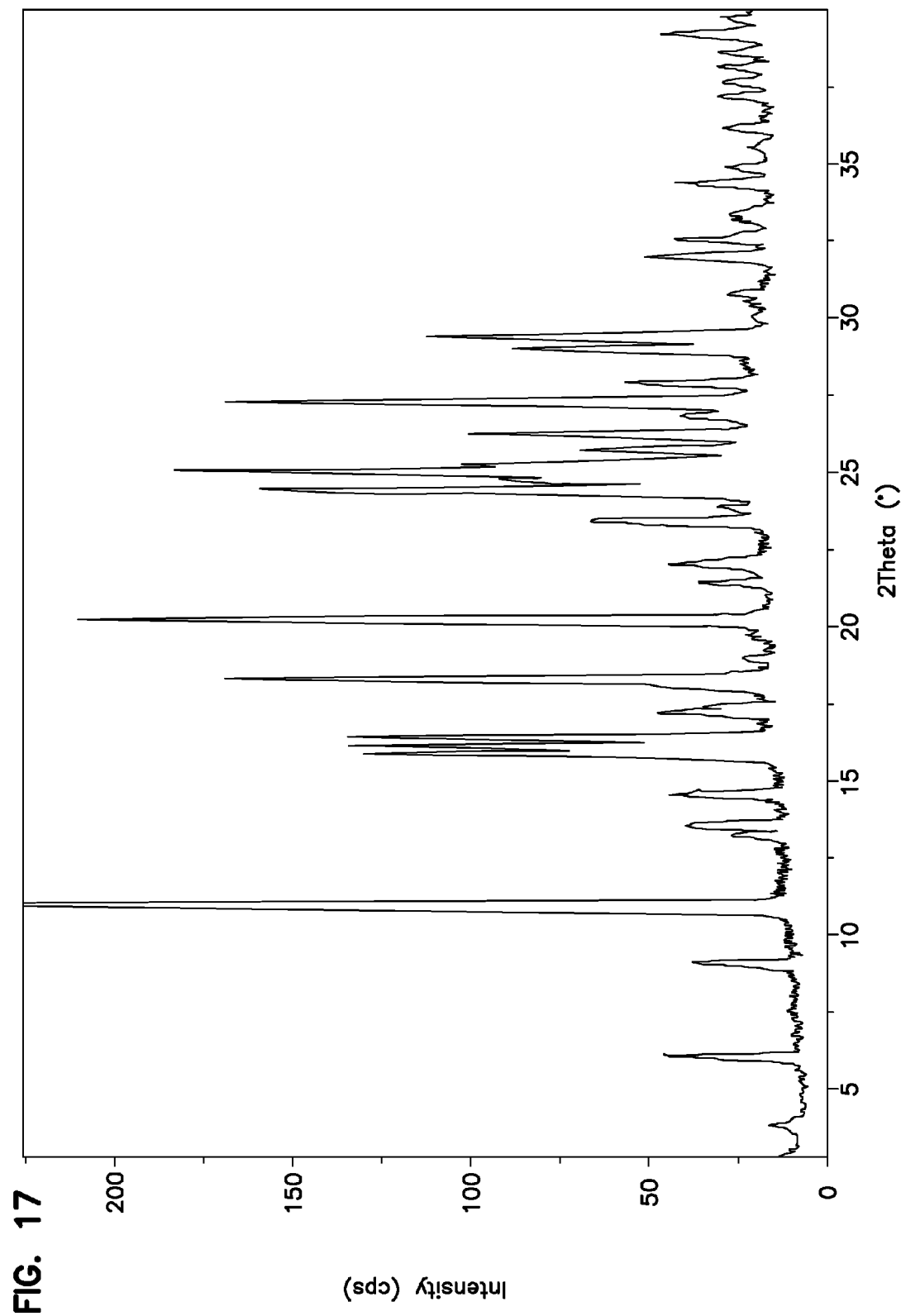
FIG. 17 shows a powder X-ray diffraction pattern of crystalline sunitinib acetate form Beta.
Figure 21:
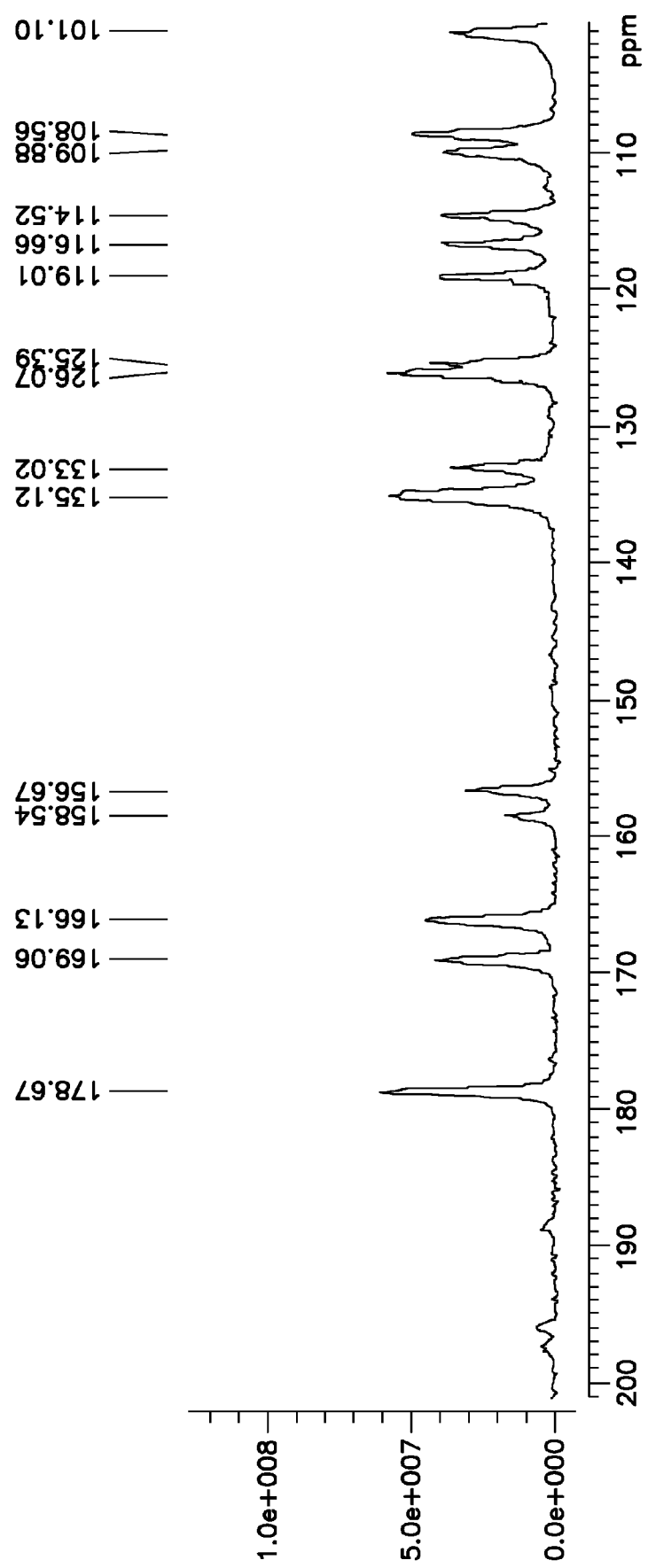
FIG. 21 shows a detailed solid state $^{13}C$ NMR spectrum of crystalline sunitinib acetate form Beta.

The second crystalline form of Sunitinib acetate is characterized by data selected from a group consisting of: a PXRD pattern having peaks at about 6.1, 11.0, 15.8, 16.4 and 20.2±0.2 degrees 2-theta, a PXRD pattern as depicted in FIG. 17, a solid-state $^{13}$C NMR spectrum having signals at about 166.1, 133.0, 119.0, 114.5, 109.9 and 108.6±0.2 ppm, a solid-state $^{13}$C NMR spectrum having chemical shifts differences between the signal exhibiting the lowest chemical shift and another in the chemical shift range of 100 to 180 ppm of about 65.0, 31.9, 17.9, 13.4, 8.8 and 7.5±0.1 ppm, a solid-state $^{13}$C NMR spectrum depicted in FIG. 21 and a combination thereof. This form can be designated as form Beta.

Typically, the signal exhibiting the lowest chemical shift in the chemical shift area of 100 to 180 ppm is at about 101.1±1.0 ppm.

Figure 18:
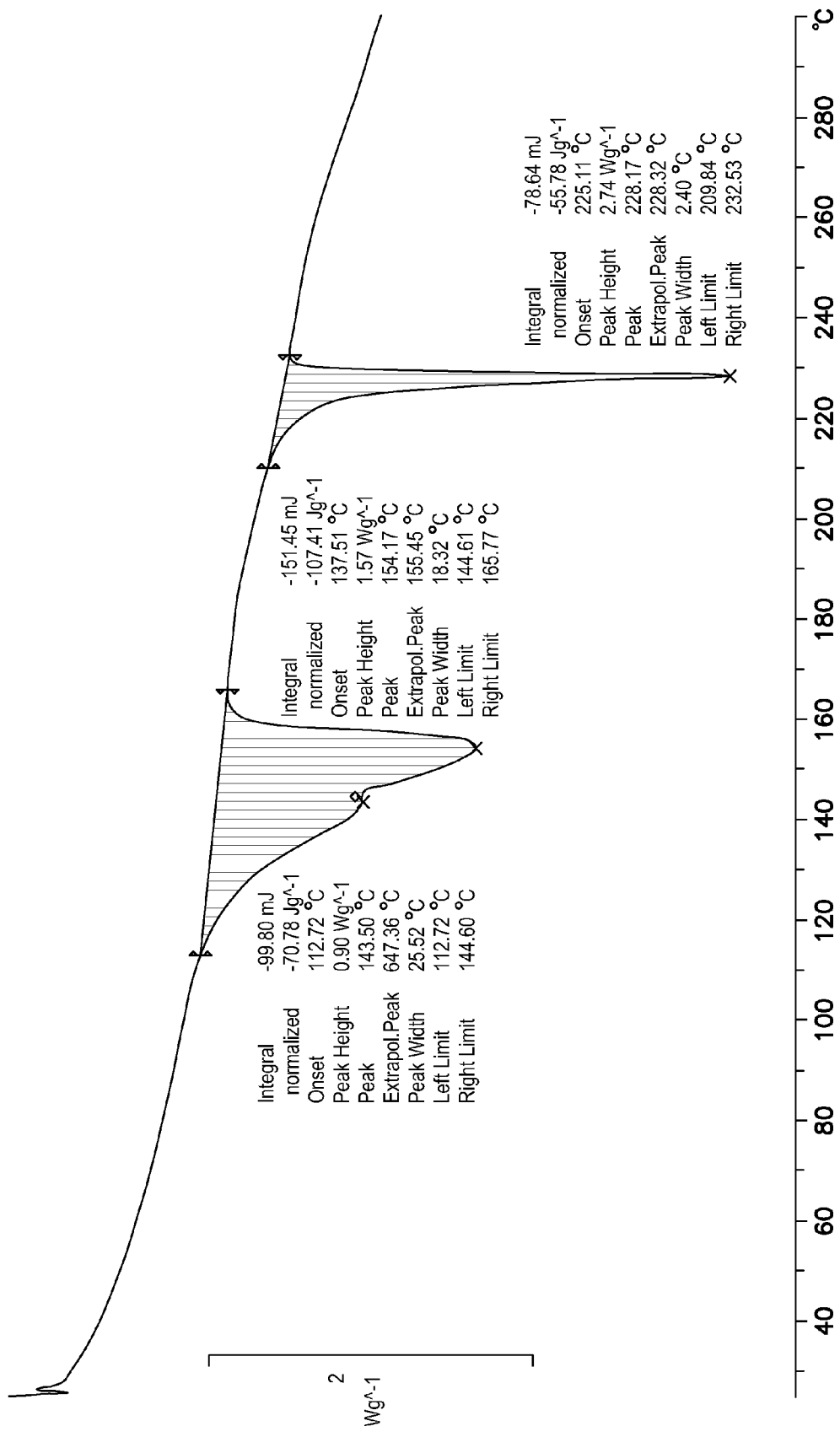
FIG. 18 shows a DSC thermogram of crystalline sunitinib acetate form Beta.
Figure 19:
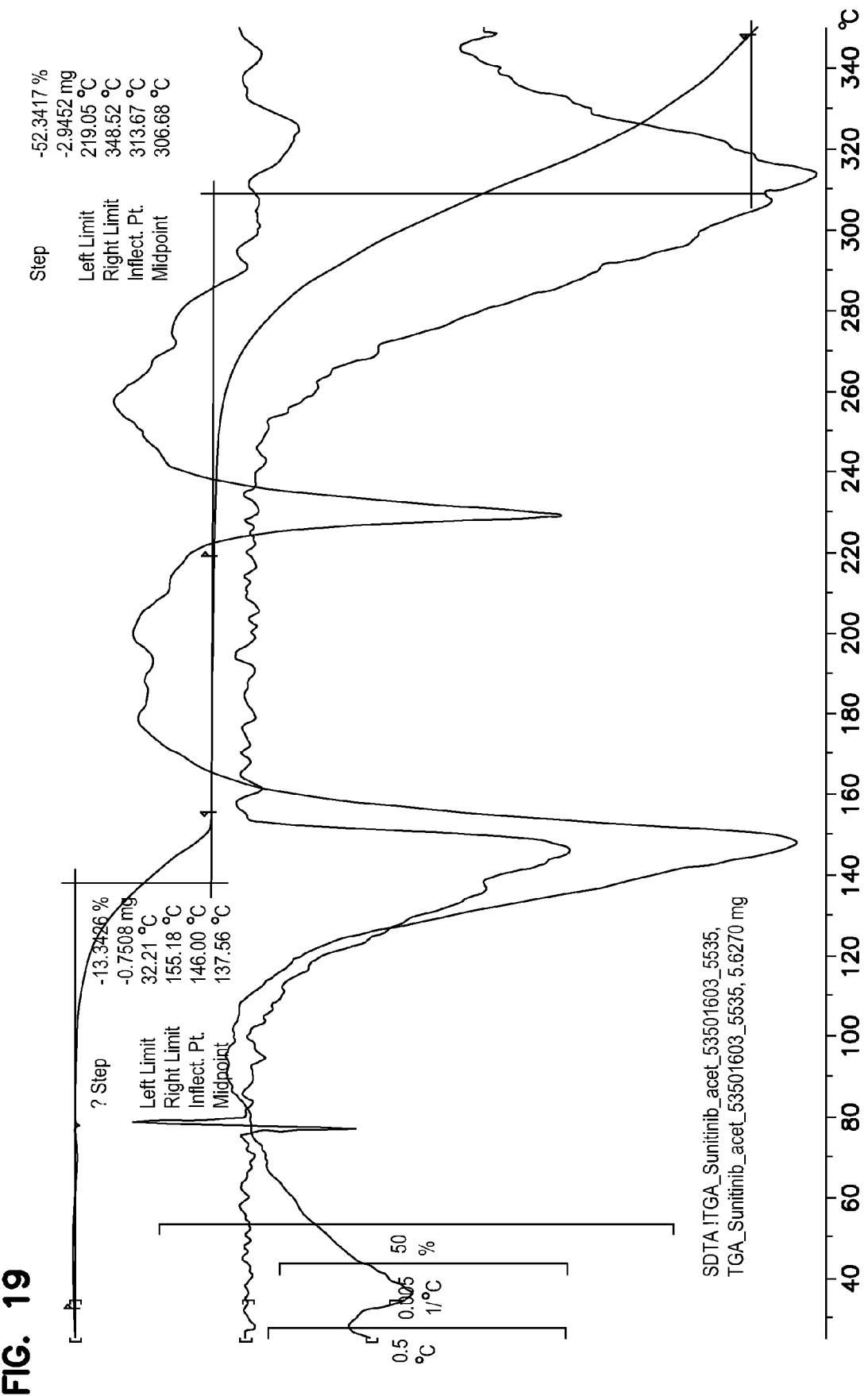
FIG. 19 shows a TGA thermogram of crystalline sunitinib acetate form Beta.

Sunitinib acetate designated form Beta can be further characterized by data selected from a group consisting of: a PXRD pattern having peaks at about 9.1, 18.2, 24.4, 25.0 and 29.3±0.2 degrees 2-theta, a DSC thermogram as depicted in FIG. 18, and a TGA thermogram as depicted in FIG. 19.

Crystalline Sunitinib acetate form Beta is anhydrous.

Preferably, the amount of acetic acid in Sunitinib acetate form beta as measured by TGA is of about 11% to about 15% by weight, more preferably, of about 12% to 14% by weight, most preferably, of about 13% by weight.

The above crystalline forms of Sunitinib acetate can be prepared by a process comprising providing a mixture containing Sunitinib base, acetic acid and a solvent, wherein from this mixture crystalline Sunitinib acetate precipitates, when more than about 5 mole equivalents of acetic acid per mole equivalents of Sunitinib base are used, form Alpha is obtained and when about 1 to about 2 mole equivalents of acetic acid per mole equivalents of Sunitinib base are used, form Beta is obtained.

Typically, the said mixture is obtained by providing a solution of Sunitinib base and acetic acid in a solvent, and then precipitating the said crystalline form.

The solution can be prepared by dissolving isolated sunitinib base in the solvent and combining with acetic acid or by combining the reaction mixture where Sunitinib base is formed with acetic acid; preferably, the mixture contains also the solvent. This mixture can be provided, preferably by reacting Sunitinib acyl chloride derivative and 2-diethylaminoethylamine providing Sunitinib base.

Preferably, the solvent is selected from a group consisting of n-butanol, a mixture of diisopropyl ether and methyl tert buthyl ether ("MTBE"), a mixture of ethanol and MTBE, a mixture of n-butanol and MTBE and combination thereof.

Preferably, when about 5 to about 14 mole equivalents of acetic acid per mole equivalents of Sunitinib base are used, form Alpha is obtained.

Optionally, the solution can be heated to a temperature of about 45° C. to about 65° C., more preferably, of about 60° C. to about 50° C. before inducing precipitation.

Precipitation can be induced by either maintaining the said solution or by addition of an anti solvent to the said solution, for example MTBE, or by addition of an anti solvent followed by cooling.

Preferably, maintaining is done by stirring the said solution for a period of about 60 minutes, during which the crystalline form precipitates.

Preferably, cooling is done to a temperature of about −15° C. to about 5° C., more preferably, to about −10° C.

Preferably, the said solution can be further cooled after the precipitation to a temperature of about −15° C. to about 5° C., more preferably, to about −10° C.

The process for preparing the crystalline form of sunitinib acetate may further comprise recovery of the said crystalline form from the suspension. The recovery may be done, for example, by filtering the suspension comprising sunitinib acetate form Alpha, washing and drying. Preferably, washing is done with methyl tert-butyl ether ("MTBE"). Preferably, drying is done on air. Preferably, drying is performed at a temperature of about 20° C. to about 25° C., more preferably, at about 20° C. Preferably, drying is done for a period of about 1 to 12 hours, more preferably, for about 1 to about 3 hours.

The obtained crystalline forms Alpha and Beta can be further slurried in MTBE to purify the said crystalline form.

Sunitinib acetate and its crystalline forms can be used to prepare sunitinib malate, preferably, sunitinib malate form 1, for example as demonstrated below.

In another embodiment, the present invention encompasses a process for preparing Sunitinib malate comprising preparing Sunitinib acetate and crystalline forms according to the processes of the present invention and converting them to Sunitinib malate, for example as mentioned above. Preferably, sunitinib acetate and crystalline forms thereof are prepared according to any embodiment of the processes of the present invention.

The obtained Sunitinib malate is characterized by diffraction peaks at about 13.2 and 24.2 degrees two-theta ("form 1").

In addition, crystalline form 1 can be prepared by another process comprising providing a mixture comprising sunitinib malate and a solvent selected from the group consisting of pyridine, dioxane, butyl acetate, ethyl acetate, dimethylformamide, a mixture of dimethylacetamide and n-propanol, a mixture of N-methyl-pyrrolidone ("NMP") and toluene, dimethylsulfoxide ("DMSO"), a mixture of DMSO and ethylacetate, isopropanol, a mixture of NMP and n-propanol, a mixture of methanol and water, a mixture of water, ethanol and acetone, NMP, 2-methyltetrahydrofuran, water, ethanol, methanol and mixtures thereof.

In a preferred embodiment, when the solvent is selected from a group consisting of: dioxane, butyl acetate, ethyl acetate or mixtures thereof, the mixture is preferably a suspension which is provided by a process comprising reacting Sunitinib base and malic acid in the solvent, to obtain the said suspension comprising the crystalline form.

First, Sunitinib base, malic acid and a solvent as mentioned above are combined providing a suspension. Then, the suspension is heated to obtain the said mixture comprising the crystalline form 1 of sunitinib malate. Preferably, the heating is done to a temperature of about 60° C. to about 120° C.

Optionally, the said mixture is cooled prior to recovering the crystalline form 1 of sunitinib malate. Preferably, the cooling is done to a temperature of about 25° C. to about 20° C.

In another preferred embodiment, when the solvent is pyridine the mixture is a solution which is provided by a process comprising reacting sunitinib base and malic acid in pyridine.

Preferably, sunitinib base is dissolved in pyridine prior to reacting with malic acid.

Preferably, the dissolution of sunitinib base in pyridine is done at a temperature of about 95° C. to 105° C. More preferably, the dissolution is done to a temperature of about 100° C.

The solution is then combined with malic acid, preferably, L-malic acid providing a second solution. The crystalline form 1 then precipitates from the solution providing the said mixture from which it is recovered.

Preferably, precipitation is induced by maintaining the second solution. Preferably, the solution is maintained at a temperature of about 20° C., preferably, for a period of about overnight.

In another preferred embodiment, when the solvent is a mixture of methanol and water, the mixture is preferably a suspension which is provided by a process comprising reacting Sunitinib base and malic acid in the said solvent.

First, Sunitinib base is suspended in methanol, and then the suspension is combined with malic acid providing a second suspension from which form 1 is recovered. Preferably, malic acid is added in a form of a solution in water.

Preferably, the reaction between sunitinib base and malic acid is done at room temperature.

In another embodiment, when the solvent is selected from a group consisting of: a mixture of dimethylacetamide and n-propanol, a mixture of N-methyl-pyrrolidone ("NMP") and toluene, and a mixture of N-methyl-pyrrolidone ("NMP") and n-propanol the said mixture is provided by a process comprising reacting Sunitinib base and malic acid in the said solvent providing sunitinib malate, which precipitates by admixing the solution with an anti solvent selected from the group consisting of n-propanol, toluene, ethyl acetate and mixtures thereof.

Preferably, the precipitated crystalline form 1 is then recovered.

Preferably, sunitinib base, the solvent and malic acid are combined to obtain a mixture, which is then optionally heated, providing the said solution. Preferably the heating is done to a temperature of about 35° C. to about 60° C. More preferably, to a temperature of about 40° C.

Further, the anti solvent is added to the solution to obtain the said mixture, which is a suspension. Preferably, the anti solvent is added at a temperature of about 35° C. to about 40° C. more preferably, at a temperature of about 20° C. to about 40° C.

Optionally, the suspension is maintained at the same temperature for a period of about 30 minutes to about 3 hours. More preferably, for a period of about 1 to 1.5 hours. Most preferably, for a period of about 1 hour.

Then, the said suspension is cooled to a temperature of about 10° C. to about 0° C., more preferably, to about 0° C. prior to recovering the said form.

In another preferred embodiment, when the solvent is a combination of water, ethanol and acetone the said mixture, which is a suspension, is provided by a process comprising crystallizing sunitinib malate from a mixture of water as a solvent and a mixture of ethanol and acetone as anti solvent.

First, Sunitinib malate is dissolved in water providing a solution. Then ethanol and acetone are added to the solution providing a second solution from which crystalline form 1 of sunitinib malate precipitates, and then can be recovered.

The second solution can be maintained to allow precipitation of sunitinib malate form 1. Preferably, the solution is maintained at a temperature of about 40° C., preferably for a period of about overnight.

In another preferred embodiment, when the solvent is N-methyl-pyrrolidone ("NMP") the said mixture, which is a suspension, is provided by a process comprising crystallizing sunitinib malate from N-methyl-pyrrolidone ("NMP").

First, Sunitinib malate is dissolved in N-methyl-pyrrolidone ("NMP") providing a solution. Preferably, dissolution is done by heating to a temperature of about 100° C.

Preferably, the heated solution is cooled to allow precipitation of crystalline form 1 of sunitinib malate.

Preferably, the precipitation is done for a period of about overnight.

The above processes for preparing the said crystalline sunitinib malate form 1 may further comprise recovering the crystalline sunitinib malate form 1 from the said mixture. The recovery may be done for example, by filtering the mixture, and drying. Preferably, drying is done at a temperature of about 40° C. to about 70° C., preferably, for a period of about 16 hours to about 20 hours.

In yet another preferred embodiment, when the solvent is selected from a group consisting of: water, methanol, ethanol and mixtures thereof the said mixture is provided by a process comprising slurring composition L containing Sunitinib base and L-malic acid in the said solvent.

Preferably, the slurry is maintained for a period of about 3 days, prior to recovering the crystalline form. Preferably, the slurry is maintained until the solvent is completely removed.

In yet another preferred embodiment, when the solvent is methanol the said mixture can also be provided by a process comprising mixing the powdery crystalline Sunitinib base form VIII and powdery crystalline L-malic acid to obtain a mixture of both powders, and combining the said mixed powder with methanol to obtain sunitinib malate form 1.

Preferably, both powders are grounded separately prior to mixing them. Preferably, when mixed, a homogenizing powder is formed. Preferably, grounding is done in mortar by means of pestle. Preferably, homogenizing is done by shaking.

The said powder is then combined with methanol, and the mixture is maintained for a period of about 3 days to obtain sunitinib malate form 1.

The crystalline Sunitinib malate form 1 can also be prepared by a process comprising suspending composition containing Sunitinib base and L-malic acid selected from a group consisting of composition F, G, H, I, K, O, P and Q and mixtures thereof in either methanol, ethanol or water, wherein when the solvent is either methanol or ethanol the composition is selected from a group consisting of composition F, G, H, I, K, O, P and Q and mixtures thereof, and when the solvent is water the composition is selected from a group consisting of composition H, I, K and mixtures thereof.

Preferably, the suspension is maintained prior to recovering the obtained crystalline form 1 of Sunitinib malate. Preferably, the suspension is maintained for a period of about 3 days. Preferably, the suspension is maintained at a temperature of about room temperature. More preferably, the suspension is maintained at a temperature of about 20° C. to about 30° C.

Composition F, G, H, I, K, O, P and Q can be prepared, for example, according to the process disclosed in WO publication No. 20090067686, hereby incorporated by reference.

Figure 22:
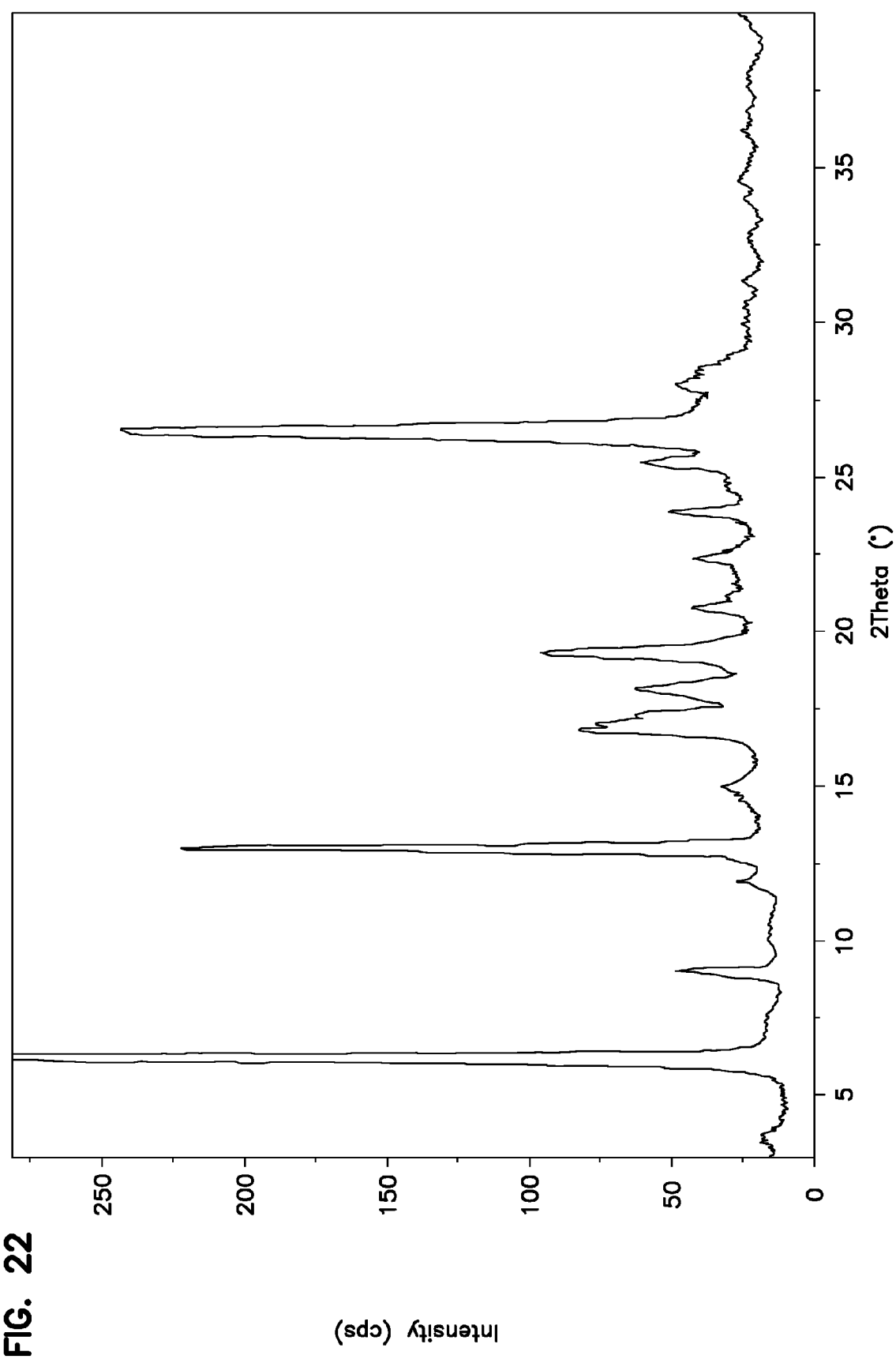
FIG. 22 shows a powder X-ray diffraction pattern of crystalline sunitinib base form XX.

In one embodiment, the present invention encompasses a crystalline form of Sunitinib base characterized by data selected from a group consisting of: a PXRD pattern having peaks at about 6.2, 9.0, 13.0, 19.3 and 22.4±0.2 degrees 2-theta, a PXRD pattern as depicted in FIG. 22. This form can be designated as form XX.

Sunitinib base form XX can be further characterized by data selected from a group consisting of: a PXRD pattern having peaks at about 11.9, 18.1, 23.8 and 25.4±0.2 degrees 2-theta.

Preferably, the amount of acetic acid in crystalline Sunitinib base form XX is not more than 0.5% w/w as determined by solution $^1$H NMR.

The above crystalline form of Sunitinib base form XX can be prepared by a process comprising drying Sunitinib acetate form alpha at a temperature of about 120° C.

The above crystalline form of Sunitinib base form XX can be also prepared by a process comprising crystallizing Sunitinib acetate form Alpha from either MTBE or a mixture of ethanol and MTBE and drying the obtained crystalline form at a temperature of about 75° C.

Preferably, drying is done under vacuum.

Typically, in the current process acetic acid is evaporated thus leading to crystalline Sunitinib base that contains not more than 0.5% w/w of acetic acid.

Figure 23:
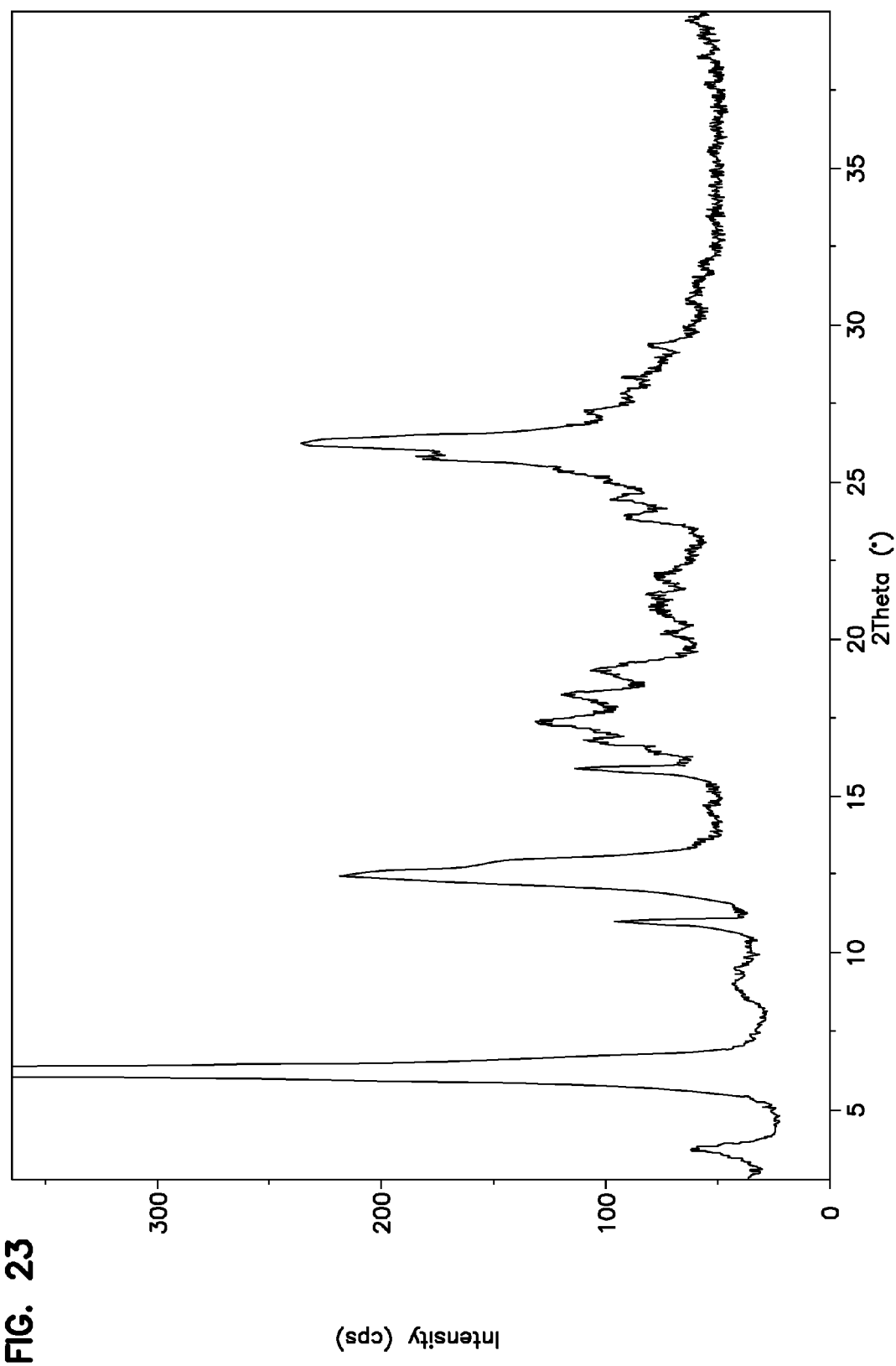
FIG. 23 shows a powder X-ray diffraction pattern of crystalline sunitinib base form XXI.

In one embodiment, the present invention encompasses a crystalline form of Sunitinib base characterized by data selected from a group consisting of: a PXRD pattern having peaks at about 6.2, 10.9, 12.4, 15.9 and 26.2±0.2 degrees 2-theta, a PXRD pattern as depicted in FIG. 23. This form can be designated as form XXI.

Sunitinib base form XXI can be further characterized by data selected from a group consisting of: a PXRD pattern having peaks at about 3.7, 17.3, 18.2 and 19.0±0.2 degrees 2-theta.

Preferably, the amount of acetic acid in Sunitinib base form XXI is not more than 0.5% w/w as was determined by solution $^1$H NMR.

The above crystalline form of Sunitinib base form XXI can be prepared by a process comprising crystallizing Sunitinib acetate from a mixture comprising ethanol and diisopropyl ether and drying the obtained crystalline form at a temperature of about 75° C.

Preferably, drying is done under vacuum.

Figure 24:
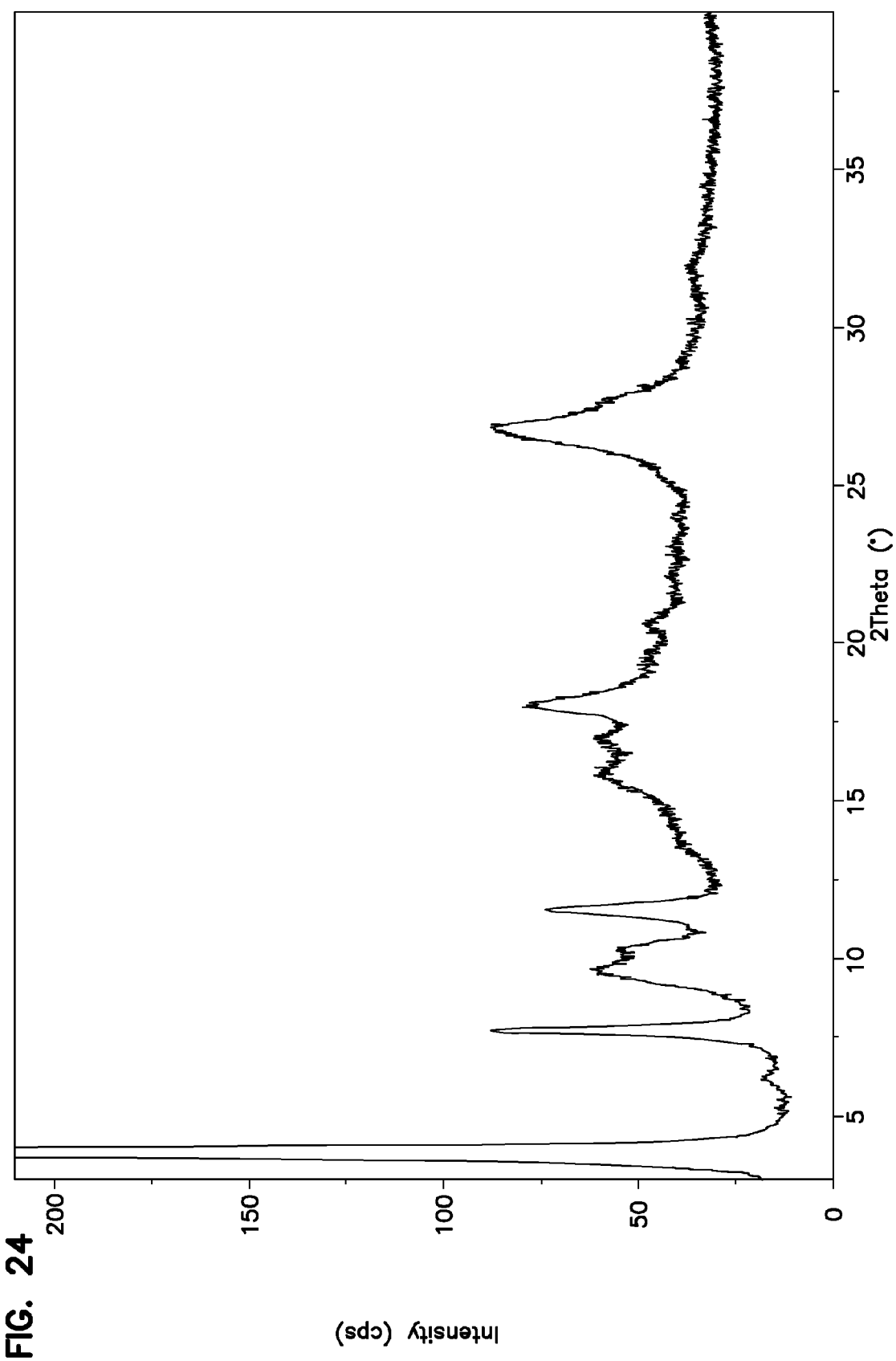
FIG. 24 shows a powder X-ray diffraction pattern of crystalline sunitinib base form XXII.

In one embodiment, the present invention encompasses a crystalline form of Sunitinib base characterized by data selected from a group consisting of: a PXRD pattern having peaks at about 3.8, 7.7, 11.5, 18.0 and 26.7±0.2 degrees 2-theta, a PXRD pattern as depicted in FIG. 24. This form is designated as form XXII.

Sunitinib base form XXII can be further characterized by data selected from a group consisting of: a PXRD pattern having peaks at about 9.6, 10.3, 15.8 and 16.9±0.2 degrees 2-theta.

Preferably, the amount of acetic acid in Sunitinib base form XXII is not more than 0.5% w/w as was determined by solution $^1$H NMR.

The above crystalline form of Sunitinib base form XXII can be prepared by a process comprising drying Sunitinib acetate form beta.

Preferably, drying is done by heating Sunitinib acetate form beta at a temperature of about 120° C. Preferably, drying is done under vacuum.

EXAMPLES

PXRD

XRD diffraction was performed on X-Ray powder diffractometer: Philips X'pert Pro powder diffractometer, CuKα radiation, λ=1.5418 Å. X'Celerator detector active length (2 theta)=2.122 mm, laboratory temperature 22-25° C. Zero background sample-holders were used. Prior to analysis the samples were gently ground by means of mortar and pestle in order to obtain a fine powder. The ground sample was adjusted into a cavity of the sample holder and the surface of the sample was smoothed by means of a cover glass.

Measurement parameters:
Scan range: at least 4-40° 2-theta;
Scan mode: continuous;
Step size: 0.0167°;
Time per step: 21 s;
Sample spin: 16 rpm;
Sample holder: quartz plate.

DSC

DSC measurements were performed on Differential Scanning Calorimeter DSC823e (Mettler Toledo). Alumina crucibles 40 μl with PIN were used for sample preparation. Usual weight of sample was 1.5-3.5 mg. Program: temperature range from at most 40° C. to at least 300° C., heating rate 10° C./min, nitrogen flow 50 ml/min.

TGA

TGA measurements were performed on Thermo gravimetric analyzer TGA851e (Mettler Toledo). Alumina crucibles 70 μl were used for sample preparation. Usual weight of sample was 7-13 mg. Program: temperature range at most 40° C. to at least 300° C., heating rate 10° C./min, nitrogen flow 50° C./min.

Solid-State $^{13}$C NMR

All $^{13}$C CP/MAS NMR spectra were measured at 125 MHz using Bruker Avance 500 WB/US NMR spectrometer (Karlsruhe, Germany, 2003) at magic angle spinning (MAS) frequency 11 kHz. In all cases finely powdered samples were placed into the 4 mm ZrO$_2$ rotors and standard CPMAS pulse program was used. During acquisition of the data a high-power dipolar decoupling TPPM (two-pulse phase-modulated) was applied. The phase modulation angle was 15°, and the flip-pulse length was 4.8 μs. Applied nutation frequency of B$_1$($^1$H) field was 89.3 kHz. Nutation frequency of B$_1$($^{13}$C) and B$_1$($^1$H) fields during cross-polarization was 62.5 kHz and repetition delay was 4 s. The number of scans was 3600 consequently the total experimental time was about 4 hours. The $^{13}$C scale was calibrated with glycine as external standard (176.03 ppm-low-field carbonyl signal).

The NMR spectrometer was completely calibrated and all experimental parameters were carefully optimized prior the investigation. Magic angle was set using KBr during standard optimization procedure and homogeneity of magnetic field was optimized using adamantane sample (resulting linewidth at half-height Δv$_{1/2}$ was less than 3.5 Hz at 250 ms of acquisition time). Taking into account frictional heating of the samples during fast rotation all NMR experiments were preformed at 305 K (precise temperature calibration was performed).

Solution $^1$H NMR

Instrument: Bruker Avance III (400.13 MHz for $^1$H, 100.61 MHz for $^{13}$C, DMSO-d$_6$, 30° C.). The ratio of acetic acid/sunitinib was determined by recording proton spectra and integrating the upper region where the signals of ethyl (1 ppm, 6H) and acetyl (1.9 ppm, 3H) groups appear.

Example 1

Preparation Sunitinib Malate Form 1

Sunitinib base (600 mg) was dissolved in pyridine (5 ml) at 100° C. and L-malic acid (230 mg) was added to the hot solution. Slight heating provided clear solution. Sunitinib malate was formed overnight at 20° C.

Example 2

Preparation Sunitinib Malate Form 1

To sunitinib base (300 mg) and L-malic acid (101 mg) was added dioxane (10 ml) and the slurry was heated 10 min to reflux temperature facilitating formation of sunitinib malate form 1 (374 mg).

Example 3

Preparation Sunitinib Malate Form 1

Sunitinib base (300 mg), L-malic acid (101 mg) and butyl acetate (10 ml) were heated to reflux 10 min. The suspension was allowed to cool to RT, filtered, washed with n-hexane and dried on air.

Example 4

Preparation Sunitinib Malate Form 1

To Sunitinib base (300 mg), L-malic acid (101 mg), and AcOEt (10 ml) are added, the mixture is heated to 77 C for 10 min, after precipitation the obtained solid is filtered, dried on air.

Example 5

Preparation Sunitinib Malate Form 1

1 g of sunitinib base was dissolved in 3 ml of N-methyl pyrrolidone, at RT 0.336 g of Malic acid added (as a solid): the solution was heated to 40° C. than 15 ml of toluene was added and precipitation was observed. The suspension was kept at 40° C. for 1 hour than cooled to 0° C., filtered and washed with toluene. Dried at 60° C. under vacuum for 16 h.

Example 6

Preparation Sunitinib Malate Form 1

2 g of sunitinib base were suspended in 6 ml of NMP under stirring at RT. 0.673 g of Malic acid were added to the mixture and the temperature was set at 40° C. 40 ml n-propanol were dropped in 30 minutes, the suspension was cooled to 0° C., filtered and washed with 10 ml n-propanol. Dried at 70° C. under vacuum for 16 h.

Example 7

Preparation Sunitinib Malate Form 1

2 g of sunitinib base were suspended in 6 ml of DMA under stirring at RT. 0.673 g of Malic acid were added to the mixture and the temperature was set at 40° C. 40 ml n-propanol were dropped in 30 minutes, the suspension was cooled to 0° C., filtered and washed with 10 ml n-propanol. Dried at 70° under vacuum for 16 h.

Example 8

Preparation Sunitinib Malate Form 1

5 g of sunitinib base were suspended in 100 ml of methanol. 1.684 g of Malic acid dissolved in 15 ml of water was added at RT. A partial dissolution of the mixture was observed and after 5 minutes there was the formation of a precipitate. The suspension was filtered and washed with 50 ml methanol. Dried at 50° C. under vacuum for 16 h.

Example 9

Preparation Sunitinib Malate Form 1

1 g of sunitinib base was suspended in 20 ml of methanol. 0.332 g of Malic acid dissolved in 3 ml of water was added at RT. A partial dissolution of the mixture was observed and after 5 minutes there was the formation of a precipitate. The suspension was filtered and washed with 10 ml methanol. Dried at 50° C. under vacuum for 16 h.

Example 10

Preparation Sunitinib Malate Form 1

0.5 g of Sunitinib Malate were dissolved in 3.5 g of water at 80° C., diluted with 3.5 g of ethanol and 7 g of acetone, left to crystallize overnight at RT, filtered and washed with acetone. Dried at 40° C. under vacuum for 20 hours.

Example 11

Preparation Sunitinib Malate Form 1

0.5 g of Sunitinib Malate were dissolved in 3.5 g of NMP at 100° C., then left to slowly crystallize overnight at RT. Crystals were filtered and washed with hexane. Dried at 40° C. under vacuum for 20 hours.

Example 12

Preparation Sunitinib Malate Form 1

Composition L containing Sunitinib base and L-malic acid (10 mg) was weighed into a vial, then 10 µL of water was added and the blend was mixed by shaking the vial. The vial was closed and left at ambient temperature for 3 days until drying, obtaining form 1.

Example 13

Preparation Sunitinib Malate Form 1

Composition L containing Sunitinib base and L-malic acid (10 mg) was weighed into a vial, then 10 µL of methanol was added and the blend was mixed by shaking the vial. The vial was closed and left at ambient temperature for 3 days until drying, obtaining form 1.

Example 14

Preparation Sunitinib Malate Form 1

Composition L containing Sunitinib base and L-malic acid (10 mg) was weighed into a vial, then 10 µL of ethanol was added and the blend was mixed by shaking the vial. The vial was closed and left at ambient temperature for 3 days until drying, obtaining form 1.

Example 15

Preparation Sunitinib Malate Form 1

A mixture (280 mg) of Sunitinib base (form VIII and L-malic acid in molar ratio 1:1 was prepared. The aforementioned Sunitinib base and L-malic acid were powdered separately by a mortar and pestle. The powdered Sunitinib base (210 mg) was weighed into a vial, and then the powdered L-malic acid (70 mg) was added into the same vial. The mixture was then homogenized by means of shaking the vial in hand. The mixture (10 mg) was weighed into a vial, then 10 μL of methanol was added and the blend was mixed by shaking the vial. The vial was closed and left at ambient temperature for 3 days until drying, obtaining form 1.

Example 16

Preparation Sunitinib Malate Form 1

1 g of sunitinib base was suspended in 4 ml of DMSO, at RT. 0.336 g of Malic acid added (as a solid) obtaining a solution, then 20 ml of ethyl acetate were added drop wise and precipitation was observed. The suspension was kept at 20-25° C. for 1 hour then filtered and washed with ethyl acetate. Dried at 80° C. under vacuum for 16-18 h affording 1.03 g of Sunitinib Malate.

Example 17

Preparation Sunitinib Malate Form 1

In a 250 ml reactor 0.672 g (1 eq) of L-Malic acid were loaded and dissolved into 40 ml of absolute ethanol at room temperature.

The mixture was heated to 60° C. It was thus prepared a solution of Sunitinib acetate in the following way: 2 g Sunitinib Base (1 eq) was suspended in 10 ml of water, then 0.30 g (1 eq) of acetic acid were added under stirring thus obtaining a solution. This solution was added dropwise to the solution of malic acid in ethanol at 60° C. After 10 minutes at 60° C. the mixture was cooled to 0° C. in 2 hours and left stirring at this temperature for another hour. The obtained solid was filtered on gooch P3 and washed with 3×5 ml of ethanol.

It was dried in oven under vacuum at 80° C. for 18 hours yielding 2.21 g of Sunitinib Malate.

Examples 18(a)-(h)

Preparation Sunitinib Malate Form 1

Composition F, G, H, I, K, O, P or Q containing Sunitinib base and L-malic acid (10 mg) was poured into a glass vial and about 10 μl of methanol was added. The vial was closed and the suspension was left at ambient temperature for 3 days until drying, obtaining form 1.

Examples 19(a)-(h)

Preparation Sunitinib Malate Form 1

Composition F, G, H, I, K, O, P or Q containing Sunitinib base and L-malic acid. (10 mg) was poured into a glass vial and about 10 μl of ethanol was added. The vial was closed and the suspension was left at ambient temperature for 3 days until drying, obtaining form 1.

Examples 20(a)-(c)

Preparation Sunitinib Malate Form 1

Composition H, I or K containing Sunitinib base and L-malic acid. (10 mg) was poured into a glass vial and about 10 μl of water was added. The vial was closed and the suspension was left at ambient temperature for 3 days until drying, obtaining form 1.

Example 21

Preparation Sunitinib Malate Form 1

In a 250 ml reactor 0.74 g (1.1 eq) of L-Malic acid were loaded and dissolved into 40 ml of absolute ethanol at room temperature.

The mixture was heated to 60° C. It was thus prepared a solution of Sunitinib Formate in the following way: 2 g Sunitinib Base (1 eq) was suspended in 10 ml of water, then 0.24 g (1.05 eq) of formic acid were added under stirring thus obtaining a solution. This solution was added drop wise to the solution of malic acid in ethanol at 60° C. After 10 minutes at 60° C. the mixture was cooled to 0° C. in 2 hours and left stirring at this temperature for another hour. The obtained solid was filtered on gooch P3 and washed with 3×5 ml of ethanol.

It was dried in oven under vacuum at 80° C. for 18 hours yielding 2.1 g of Sunitinib Malate.

Example 22

Preparation Sunitinib Malate Form 1

A solution of Sunitinib acetate was prepared in the following way: 10 g Sunitinib Base (1 eq) was suspended in 50 ml of water, then 1.58 g (1.05 eq) of acetic acid was added under stirring obtaining a solution. This solution was heated to 60° C. Then 160 ml of ethanol were added at this temperature.

3.7 g (1.1 eq) of L-Malic acid were dissolved into 40 ml of absolute ethanol at room temperature. This solution was added to the solution of Sunitinib acetate at 60° C. After 10 minutes at 60° C. the mixture was cooled to 0° C. in 2 hours and left stirring at this temperature for another hour. The obtained solid was filtered on gooch P3 and washed with 3×50 ml of ethanol.

It was dried in oven under vacuum at 80° C. for 18 hours yielding 12.4 g of Sunitinib Malate.

Example 23

Preparation Sunitinib Malate Form 1

3 g Sunitinib Base (1 eq) was suspended in 9 ml (3 vol) of acetic acid, obtaining a solution. This solution was heated to 40° C. Then 33 ml (11 vol) of absolute ethanol are added at this temperature and the solution was heated to 60° C.

1.1 g (1.1 eq) of L-Malic acid were dissolved into 3 ml of absolute ethanol at room temperature. This solution is added to the solution of Sunitinib acetate at 60° C.

After 15 minutes at 60° C. the mixture is cooled to 0° C. in 3 hours and left stirring at this temperature for another hour. The obtained solid is filtered on gooch P3 and washed with 3×6 ml of ethanol.

It was dried in oven under vacuum at 60° C. for 18 hours yielding 3.37 g of Sunitinib Malate (84% yield and 99.85% purity by HPLC).

Example 24

Preparation of Sunitinib Acetate Form Alpha

Sunitinib base (1.5 g) was suspended in n-butanol (7.5 ml) and acetic acid (2.3 ml) was added in one portion with stirring at 20° C. Adding of acetic acid facilitated complete dissolution of sunitinib base within 2 minutes. The solution was stirred for 60 minutes during which orange precipitate was formed. The precipitate was recovered by filtration, washed with t-butyl methyl ether (50 ml) and dried on air for 12 h at 20° C. (Yield 1.074 g).

Example 25

Preparation of Sunitinib Acetate Form Alpha

Sunitinib base (1.3 g) was dissolved in acetic acid (10 ml) by stirring for 5 min at 20° C. Then diisopropyl ether (20 min) was added within 30 min with stirring. Then the solution was filtered and t-butyl methyl ether (50 ml) was added to the stirred solution within 5 min. The orange precipitate thus formed was recovered by filtration, washed with t-butyl methyl ether (50 ml) and dried on air for 12 h at 20° C. (Yield 1.425 g).

Example 26

Preparation of Sunitinib Acetate Form Alpha

Sunitinib base (3 g) was dissolved in acetic acid (6 ml) and absolute ethanol (6 ml) by stirring for 10 min at 20° C. and the solution was heated to 50° C. Then methyl tert-butyl ether (60 ml) was added within 30 min with stirring, the mixture was cooled to −10° C. After 16 h at −10° C. the solid was filtered, washed with 2×20 ml of MTBE, dried on filter for one hour obtaining a red solid.

Example 27

Preparation of Sunitinib Acetate Form Alpha 1.5 g of the solid obtained in example 26, was slurried at 25° C. with 25 ml of MTBE for 30 minutes, then it was filtered on gooch P3 and dried on filter for one hour.

Example 28

Preparation of Sunitinib Acetate Form Beta

Sunitinib base (3 g) was suspended in n-butanol (15 ml) with stirring at 20° C., then 1.05 eq (0.45 ml) of acetic acid were added observing dissolution and after 1-2' precipitation of an orange solid. The mixture was heated to 60° C. and other 6 ml of n-butanol were added. Then methyl tert-butyl ether (60 ml) was added at 60° C. within 10 min with stirring, the mixture was cooled to −10° C. in 2 hours. After 1 h at −10° C. the solid was filtered, washed with 2×20 ml of MTBE and dried on the filter for 1 h.

Example 29

Preparation of Sunitinib Acetate Form Beta 1.5 g of the solid obtained in example 28, was slurried at 25° C. with 25 ml of MTBE for 30 minutes, then it was filtered on gooch P3 and dried on filter for one hour.

Example 30

Preparation of Sunitinib Acetate Form Beta

Sunitinib base (3 g) was suspended in n-butanol (15 ml) with stirring at 20° C. and the mixture heated to 60° C. Then 1.05 eq (0.45 ml) of acetic acid were added observing dissolution and after 1-2' precipitation of an orange solid. Then other 6 ml of n-butanol and other 0.45 ml of acetic acid were added. Then methyl tert-butyl ether (60 ml) was added at 60° C. within 10 min with stirring, the mixture was cooled to −10° C. in 2 hours. After 16 h at −10° C. the solid was filtered, washed with 2×20 ml of MTBE and dried on the filter for 1 h.

Example 31

Preparation of Sunitinib Acetate Form Beta

Sunitinib base (4 g) was suspended in n-butanol (12 ml) with stirring at 20-25° C. Then 1.05 eq (0.45 ml) of acetic acid were added observing dissolution and after 1-2' precipitation of an orange solid. Then methyl tert-butyl ether (80 ml) was added at 20-25° C. within 10 min with stirring, the mixture was cooled to −10° C. in 2 hours. After 16 h at −10° C. the solid was filtered, washed with 2×20 ml of MTBE and dried on the filter for 1 h yielding 4 g of Sunitinib Acetate.

Example 32

Preparation of Sunitinib Acetate Form Beta 1.5 g of the solid obtained in example 30, was slurried at 25° C. with 25 ml of MTBE for 30 minutes, then it was filtered on gooch P3 and dried on filter for one hour.

Example 33

Preparation of Sunitinib Acetate

Sunitinib base (10 g, 0.025 mol) was suspended in 1-butanol (70 ml) with stirring at 20° C., then 1.05 eq (1.54 ml) of acetic acid were added observing dissolution and after about 5 minutes precipitation of an orange solid. The mixture was heated to 60° C. and methyl tert-butyl ether (200 ml) was added at 60° C. within 40 min with stirring, the mixture was cooled to −10° C. in 2 hours. After 16 h at −10° C. the solid was filtered, washed with 2×20 ml of MTBE and dried on filter for 1 h. 10.8 g of Sunitinib Acetate (94% yield) was thus obtained.

Example 34

Conversion of Sunitinib Acetate to Sunitinib Malate 10 g of Sunitinib Acetate was dissolved at 20° C. in 50 ml of water, and then 20 ml of ethanol were added. The mixture was heated to 60° C. and other 170 ml of ethanol added and stirred. Then 3.7 g of L-Malic acid dissolved into 10 ml of ethanol were added under stirring thus obtaining a solution. The solution was left stirring at 60° C. for 10-15 minutes, then the mixture was cooled to 0° C. in 2 hours and left stirring at this temperature for another hour. The obtained solid was filtered on gooch P3 and washed with 2×30 ml of ethanol. The solid was dried in oven under vacuum at 50° C. for 18 hours yielding 10.8 of Sunitinib Malate (87% yield from Sunitinib Base and 99.88% purity with HPLC method).

Example 35

Conversion of Sunitinib Acetate to Sunitinib Malate 10 g of Sunitinib Acetate was dissolved at 20° C. in 50 ml of water. The mixture was heated to 60° C. and 190 ml of ethanol were added and stirred. Then 3.7 g of L-Malic acid dissolved into 10 ml of ethanol were added under stirring thus obtaining a solution. The solution was left stirring at 60° C. for 10-15 minutes, then the mixture was cooled to 0° C. in 2 hours and left stirring at this temperature for another hour. The obtained solid was filtered on gooch P3 and washed with 2×30 ml of ethanol. The solid was dried in oven under vacuum at 50° C. for 18 hours yielding 10.8 of Sunitinib Malate (87% yield from Sunitinib Base and 99.88% purity with HPLC method).

Example 36

Formation of Sunitinib Acetate Without Isolation of the Base 6 g of Sunitinib acyl chloride derivative (SAC) was loaded into the reactor and 90 ml 2-Methyltetrahydrofuran loaded and stirred. Then the reaction mixture was heated to 40° C. and 2.9 ml of 2-diethylaminoethylamine were added dropwise in five minutes at 40° C. Partial dissolution was observed then precipitation of the product occurred. After one hour the reaction was completed (until Sunitinib ester was below 2%): 90 ml of water and 2N HCl until pH 2 were added to the suspension at 40° C.

The two phases were separated at 40° C. and the organic phase discarded. The aqueous phase was washed once more with 90 ml of 2-Methyltetrahydrofuran at 40° C. under stirring. The two phases separated again and the organic phase discarded.

The aqueous phase was then basified to pH 9.0 with 5% aqueous ammonia solution at 40±2° C.

After 30 minutes stirring, the suspension was heated to 90° C., 100 ml of 1-butanol were added and complete dissolution with phase separation was observed. The two phases were separated at 90° C. and the organic phase loaded again into the reactor and concentrated under vacuum at 70° C. to residual 30 ml (5 volumes), SUN Base started to precipitate. Then the mixture was cooled to 25° C. and at this temperature 1.1 ml of acetic acid were added obtaining complete dissolution. 120 ml of MTBE were added dropwise at that temperature in about 30 minutes then the mixture was cooled to 0° C. in 2 hours, stirred for 16 hours at 0° C. and filtered on Gooch P3, washed with MTBE and the wet solid dried on filter for 4 hours.

6.4 g of Sunitinib Acetate (76% yield from SAC) were obtained with a purity of 99.5% by HPLC method.

In a reactor 30 ml of water and 6 g of Sunitinib Acetate were loaded and stirred for about 10 minutes at 25° C. The solution was heated to 40° C. and clarified by filtration on decalite pad. The solution was heated to 60° C. and 114 ml of ethanol were added in about 30 minutes. Then a solution of 1.94 g of L-Malic acid in 6 ml of ethanol was added dropwise in about 10 minutes and stirred. At the end of the addition the mixture was cooled to 35° C. in 2 hours and then stirred for 3-4 hours at the same temperature. The suspension was cooled to 0° C. in about 5 hours and then left stirring at this temperature for NLT 10 hours. The obtained solid was filtered on Gooch P3 and washed with 3×10 ml of ethanol, the wet solid was dried under vacuum at 80° C. for 16-18 hours yielding 6.2 g of Sunitinib Malate (90% yield and 99.7% purity HPLC method)

Example 37

Formation of Sunitinib Malate from Sunitinib Acetate Form Alpha

Sunitinib base (3 g) was dissolved in acetic acid (6 ml) and absolute ethanol (6 ml) by stirring for 10 min at 20° C. and the solution was heated to 50° C. Then methyl tert-butyl ether (60 ml) was added within 30 min with stirring, the mixture was cooled to −10° C. After 16 h at −10° C. the solid was filtered, washed with 2×20 ml of MTBE, dried on filter for one hour obtaining a red solid (3.1 g, 90% yield).

In a reactor 15 ml of water and 3 g of Sunitinib Acetate were loaded and stirred for about 10 minutes at 25° C. The solution was heated to 40° C. and clarified by filtration on decalite pad. The solution was heated to 60° C. and 57 ml of ethanol were added in about 30 minutes. Then a solution of 0.97 g of L-Malic acid in 3 ml of ethanol was added dropwise in about 10 minutes and stirred. At the end of the addition the mixture was cooled to 35° C. in 2 hours and then stirred for 3-4 hours at the same temperature. The suspension was cooled to 0° C. in about 5 hours and then left stirring at this temperature for NLT 10 hours. The obtained solid was filtered on Gooch P3 and washed with 3×5 ml of ethanol, the wet solid was dried under vacuum at 80° C. for 16-18 hours yielding 3.1 g of Sunitinib Malate (90% yield and 99.7% purity HPLC method).

Example 38

Preparation of Sunitinib Base Form XX

Sunitinib acetate form Alpha was heated at 120° C. in an open vial for 1 hour under vacuum 100 Pa.

Example 39

Preparation of Sunitinib Base Form XX

Sunitinib base (form D, 5 g) was dissolved in acetic acid (10 ml) and absolute ethanol (10 ml) by stirring for 5 min at 20° C. and the solution was heated to 40° C. Then methyl tert-butyl ether (100 ml) was added within 30 min with stirring, the mixture was cooled to −10° C., precipitation occurred. After 2 h at −10° C. the solid was filtered and dried for 16 hours under vacuum at 75° C. obtaining 4.8 g of orange solid.

Example 40

Preparation of Sunitinib Base Form XX

Sunitinib base (form D, 7 g) was dissolved in acetic acid (17.5 ml) by stirring for 5 min at 20° C. and the solution was heated to 45° C. Then methyl tert-butyl ether (140 ml) was added within 30 min with stirring, the mixture was cooled to −10° C., precipitation occurred. After 2 h at −10° C. the solid was filtered and dried for 16 hours under vacuum at 75° C. obtaining 5.3 g of orange solid.

Example 41

Preparation of Sunitinib Base Form XXI

Sunitinib acetate (1 g) was suspended in absolute ethanol (20 ml) under stirring at 20° C. and the mixture was heated to 40° C. Then diisopropyl ether (40 ml) was added within 10 min with stirring, the mixture was cooled to −10° C. in 2 hours and after 2 h at −10° C. the solid was filtered and dried for 16 hours under vacuum at 75° C. obtaining 0.8 g of orange solid.

Example 42

Preparation of Sunitinib Base Form XXII

Sunitinib acetate form Beta was heated at 120° C. in an open vial for 1 hour under vacuum 100 Pa.

What is claimed is:

1. A process for preparing crystalline form 1 of sunitinib malate characterized by diffraction peaks at about 13.2 and 24.2 degrees two-theta comprising reacting Sunitinib base, a weak acid and L-malic acid in alcohol or a mixture of water and alcohol, and precipitating said crystalline form 1 of Sunitinib malate.

2. The process of claim 1, wherein Sunitinib base, the weak acid and either alcohol or a mixture of water and alcohol are combined to obtain a first solution.

3. The process of claim 1, wherein the weak acid is selected from a group consisting of acetic acid, formic acid, ascorbic acid, benzoic acid, succinic acid, n-butyric acid, proionic acid and boric acid.

4. The process of claim 1, wherein the alcohol is selected form a group consisting of methanol, ethanol and isopropanol.

5. The process of claim 1, further comprising recovering the crystalline form 1 of Sunitinib malate.

* * * * *